United States Patent [19]

Poss

[11] Patent Number: 5,217,520
[45] Date of Patent: Jun. 8, 1993

[54] HERBICIDAL TRIAZOLINONES

[75] Inventor: Kathleen M. Poss, Lawrenceville, N.J.

[73] Assignee: FMC Corporation, Philadelphia, Pa.

[21] Appl. No.: 852,424

[22] Filed: Mar. 16, 1992

Related U.S. Application Data

[60] Division of Ser. No. 664,704, Mar. 5, 1991, Pat. No. 5,125,958, which is a continuation-in-part of Ser. No. 462,360, Dec. 28, 1989, abandoned, which is a continuation-in-part of Ser. No. 383,109, Jul. 20, 1989, abandoned, which is a continuation-in-part of Ser. No. 238,804, Aug. 31, 1988, abandoned.

[51] Int. Cl.$^5$ .................... A01N 43/653; A01N 57/14
[52] U.S. Cl. ................................................ 504/128
[58] Field of Search ........................... 71/92, 86

[56] References Cited

U.S. PATENT DOCUMENTS

| 4,213,773 | 7/1980 | Wolf | 71/92 |
| 4,318,731 | 3/1982 | Kajioka et al. | 71/92 |
| 4,398,943 | 8/1983 | Kajioka et al. | 71/92 |
| 4,404,019 | 9/1988 | Uematsu et al. | 71/92 |
| 4,439,229 | 3/1984 | Swithenbank | 71/96 |

FOREIGN PATENT DOCUMENTS

| 68822 | 1/1983 | European Pat. Off. |
| 3603789A1 | 8/1987 | Fed. Rep. of Germany |
| 56-53662 | 5/1981 | Japan |
| 58-225070 | 12/1983 | Japan |
| 2090250 | 7/1982 | United Kingdom |

OTHER PUBLICATIONS

PCT International Application No. WO 86/04481, published Aug. 14, 1986.
PCT International Application No. WO 85/04307, published Oct. 10, 1985.
PCT International Application No. WO 85/01637, published Apr. 25, 1985.
PCT International Application No. WO 86/02642, published May 9, 1986.
PCT International Application No. 87/00730, published Feb. 12, 1987.
PCT International Application No. WO 85/01939, published May 9, 1985.
Derwent Abstract, Accession No. 85-100678, 1985.
Derwent Abstract, Accession No. 84-090015, 1984.
Derwent Abstract, Accession No. 25467K, 1983.
Derwent Abstract, Accession No. 88-316,199, 1988.
Derwent Abstract, Accession No. 87-001,569, 1987.
Derwent Abstract, Accession No. 87-229,899, 1987.
Derwent Abstract, Accession No. 88-184,132, 1988.
Derwent Abstract, Accession No. 88-127,035, 1988.
Derwent Abstract, Accession No. 87-362,698, 1987.
Derwent Abstract, Accession No. 88-063,985, 1988.
Derwent Abstract, Accession No. 85-122,460, 1985.
Derwent Abstract, Accession No. 86-020,889, 1986.
Derwent Abstract, Accession No. 87-183,175, 1987.
Derwent Abstract, Accession No. 84-020,128, 1984.

(List continued on next page.)

*Primary Examiner*—Allen J. Robinson
*Assistant Examiner*—B. Bembenick
*Attorney, Agent, or Firm*—Stanford M. Back; Robert M. Kennedy; Norman L. Craig

[57] ABSTRACT

A herbicidal compound which is a Q-substituted 1-phenyl-4,5-dihydro-1,2,4-triazol-5(1H)-one in which the Q-substituent is bonded to the ring-carbon atom at the 5-position of the phenyl group and in which:

Q is —CH($R^2$)C($R^3$) ($R^4$)Q' or —CH=C($R^4$)Q';
$R^2$ and $R^3$ are each, independently, H or halogen;
$R^4$ is H or lower alkyl;
Q' is COOH, COOZ, COO$R^5$, CON($R^6$) ($R^7$), CN, CHO or C(O)$R^5$;
Z is a salt-forming group;
$R^5$ is alkyl, alkoxycarbonylalkyl, cycloalkyl or aralkyl;
each of $R^6$ and $R^7$ is, independently, a radical which is alkyl, cycloalkyl, alkenyl, alkynyl, alkoxy, phenyl, benzyl or SO$_2R^6$ or is one of said radicals substituted by halogen, alkyl or cyano; said compound being one whose 5-Methoxy Analogs and 5-Propargyloxy Analog are herbicides.

6 Claims, No Drawings

OTHER PUBLICATIONS

Derwent Abstract, Accession No. 84,254,501, 1984.
Derwent Abstract, Accession No. 86-133,830, 1986.
Derwent Abstract, Accession No. 86-133,831, 1986.
Derwent Abstract, Accession No. 88-088,439, 1988.
Derwent Abstract, Accession No. 88-025,708, 1988.
Derwent Abstract, Accession No. 86-133,827, 1986.
Derwent Abstract, Accession No. 84-246,947, 1984.
Derwent Abstract, Accession No. 7605J, 1982.
Derwent Abstract, Accession No. 85-181,185, 1985.
Derwent Abstract, Accession No. 44794T, 1971.
Derwent Abstract, Accession No. 88-072,656, 1988.
PCT International Application No. 87/07602, Published Dec. 17, 1987.
Chemical Abstract 105(7):60524v, 1986.

HERBICIDAL TRIAZOLINONES

This application is a division of U.S. application Ser. No. 664,704, filed Mar. 5, 1991 (now U.S. Pat. No. 5,125,958), which in turn is a continuation-in-part of application Ser. No. 462,360, filed Dec. 28, 1989 (abandoned), which in turn is a continuation-in-part of application Ser. No. 383,109, filed Jul. 20, 1989, now abandoned, which in turn is continuation-in-part of application Ser. No. 238,804, filed Aug. 31, 1988, now abandoned.

This invention relates to herbicidal 1-aryl-4,5-dihydro-1,2,4-triazol-5(1H)-ones.

The herbicidal activity of certain 1-aryl-4,5-dihydro-1,2,4-triazol-5(1H)-ones (also known as 1-aryl-$\Delta^2$-1,2,4-triazolin-5-ones) has been described in the patent literature, as discussed below.

British published patent application 2,090,250 discloses herbicidal compounds of the formula

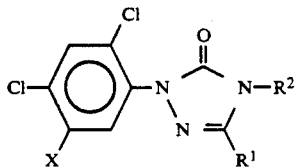

wherein $R^1$ is an alkyl group, $R^2$ is an alkynyl group, halomethyl group, or a haloethyl group and X is an alkoxy group, an alkenyloxy group, an alkoxyalkoxy group, an alkynyloxy group, a hydroxy group, a halomethyloxy group, or a haloethyloxy group.

Japanese Kokai 58-225,070 discloses herbicidal compounds of the formula

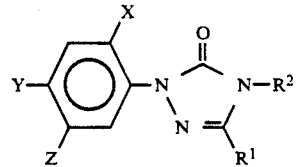

wherein $R^1$ is 1–4C alkyl; $R^2$ is H, 1–4C alkyl, halomethyl or 3–4C alkynyl; X is Cl or F; Y is Cl, Br, OH or $OR^3$; $R^3$ is 1–4C alkyl or benzyl; Z is H, carboxy, cyanomethoxy, $COOR^4$, $COSR^5$ or $CON(R^6)(R^7)$; $R^4$ is 1–4C alkyl or 3–4C alkoxyalkyl; $R^5$ is 1–4C alkyl; and $R^6$ and $R^7$ are H, 1–4C alkyl or alkoxy.

U.S. Pat. No. 4,318,731 discloses herbicidal compounds of the formula

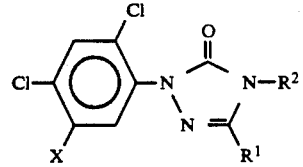

wherein $R^1$ is $C_1$–$C_4$ alkyl; $R^2$ is hydrogen, $C_1$–$C_6$ alkyl or $C_1$–$C_4$ alkenyl; and X is hydroxy, $C_1$–$C_4$ alkyl, $C_1$–$C_6$ alkyloxy, an alkyloxyalkyloxy of which two alkyls may be the same or different and each alkyl is $C_1$–$C_4$, a $C_2$–$C_4$ alkenyloxy, or an alkyloxycarbonylalkyloxy of which two alkyls may be the same or different and each alkyl is $C_1$–$C_4$.

U.S. Pat. No. 4,404,019 discloses herbicidal compounds of the formula.

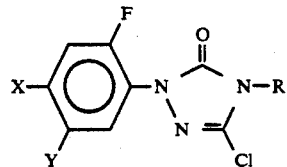

wherein R is a $C_1$–$C_4$ alkyl group, a $C_3$–$C_4$ alkenyl group or a $C_3$–$C_4$ cycloalkyl group, X is a chlorine or bromine atom and Y is a hydrogen atom or a $C_1$–$C_4$ alkoxy group.

U.S. Pat. No. 4,213,773 discloses fused-ring 1,2,4-triazolin-5-ones of the formula

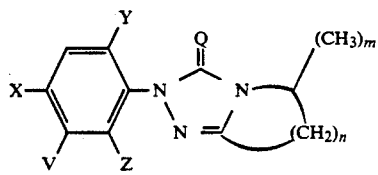

in which V may be alkyl, X is F, Cl, Br, CN, $CH_3$, $CH_3O$ or $NO_2$, Y is H, F, Cl, Br or $CH_3$, Z is H, F, Cl or Br, n is 3 to 5, m is 0–2 and Q is O or S.

PCT International Applications WO 85/01637 published Apr. 25, 1985, WO 85/04307 published Oct. 10, 1985, WO 86/04481 published Aug. 14, 1986, WO 86/02642 published May 9, 1986, and WO 87/00730 published Feb. 12, 1987 disclose various other substituted aryl-1,2,4-triazolin-5-ones in which the substituents at the 5-position of the benzene ring of the aryl group are, for instance, alkoxy, alkynyloxy, alkenyloxy, tetrahydrofuranyloxy or similar heterocycle-oxy, a group of the formula $OR^3COOR^4$ (where $R^3$ may be alkylene or haloalkylene and $R^4$ may be substituted alkyl, alkenyl, etc.), alkyl, cyanoalkyl, $COR^6$, $CH_2COR^6$ or $CH(CH_3)COR^6$ (where $R^6$ is, for instance, alkoxy or alkyl-substituted amino).

The compounds of this invention are herbicidal 1-aryl-4,5-dihydro-1,2,4-triazol-5(1H)-ones such as those in the prior art (e.g. the references mentioned above) in which, however, the carbon atom at the 5-position of the benzene ring carries a substituent (Q) as described below:

Q is a group of the formula:
—$CH(R^2)C(R^3)(R^4)Q'$ or —$CH=C(R^4)Q'$ in which Q' is a carboxylic acid group (i.e. COOH) or a salt, ester, amide, or nitrile of such carboxylic acid group. Thus Q' may be:
$CO_2H$,
$CO_2Z$,
$CO_2R^5$,
$CON(R^6)(R^7)$, or
CN.

In another aspect of this invention Q' may be an aldehydic or ketonic group, e.g. —CHO or —$COR^5$.

Z may be a salt-forming group, such as one which forms a base addition salt with a carboxylic acid, e.g. a sodium, potassium, calcium, ammonium, magnesium, or mono-, di- or tri($C_1$ to $C_4$ alkyl) ammonium or sulfonium or sulfoxonium ion.

$R^5$ may be alkyl, alkoxycarbonylalkyl, cycloalkyl (e.g. of 3 to 6 carbon atoms such as cyclopropyl or cyclopentyl), aralkyl such as benzyl or substituted benzyl (e.g. chlorobenzyl, alkylbenzyl, or haloalkylbenzyl, such as 4-chlorobenzyl or 4-trifluoromethylbenzyl).

$R^6$ and $R^7$ may each, independently, be H, OH, alkyl, cycloalkyl, alkenyl, alkynyl (e.g. propynyl), alkoxy, phenyl, benzyl, or $SO_2R^6$ (in which $R^6$ is other than H), or any of the foregoing carrying additional substituents; such additional substituents may be halogen (e.g. in haloalkyl such as chloroethyl, halophenyl such as chlorophenyl, halobenzyl such as chlorobenzyl), alkyl, or cyano.

In the foregoing formula for Q, $R^2$ and $R^3$ may each, independently, be hydrogen or halogen (such as chlorine, bromine, or fluorine), while $R^4$ may be H or lower alkyl.

The other substituents on the herbicidal 1-aryl-4,5-dihydro-1,2,4-triazol-5(1H)-ones of this invention may, for instance, be any of those present in the herbicidal aryl triazolinones of the prior art mentioned above. For instance those other substituents are so chosen that the 5-Methoxy and 5-Propargyloxy Analogs of the compounds of this invention are herbicides; the 5-Methoxy Analog of a compound of this invention has a formula which is identical with that of the compound of this invention in all respects except that the ring-carbon atom at the 5-position of the benzene ring carries a methoxy substituent instead of a substituent Q as defined above. Similarly, the 5-Propargyloxy Analog is otherwise identical except that the carbon at the 5-position of its benzene ring carries a propargyloxy substituent instead of a substituent Q as defined above. Thus the 5-Methoxy Analog of compound no. 3 of Table 1 below is 1-(2,4-dichloro-5-methoxyphenyl)-4-difluoromethyl-4,5-dihydro-3-methyl-1,2,4-triazol-5(H)-one and the 5-Propargyloxy Analog of compound no. 3 is 1-(2,4-dichloro-5-propargyloxyphenyl)-4-difluoromethyl-4,5-dihydro-3-methyl-1,2,4-triazol-5(H)-one.

The compounds of this invention preferably have 5-Methoxy Analogs and 5-Propargyloxy Analogs of marked herbicidal properties. For instance, said Analogs of the preferred compounds show at least 50% kill of at least one of the following species of plants when applied under at least one of the following modes at the rate of 0.5 kg/ha, and more preferably show such kill of at least 50% when applied at the rate of 0.1 kg/ha: Species; velvetleaf (*Abutilon theophrasti*) green foxtail (*Setaria viridis*); Modes: preemergent, postemergent. Testing for such herbicidal activity may be carried out in the manner described below under the heading "Herbicidal Activity".

Representative compounds of this invention are listed in Table 1 below.

One may describe many of the compounds of this invention by the formulas

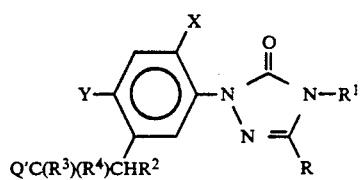

Formula I

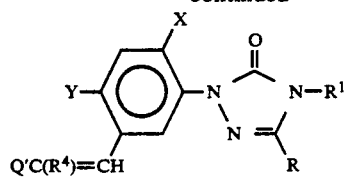

Formula II in which Q', $R^2$, $R^3$ and $R^4$ have the meanings set forth above and the substituents R and $R^1$ on the triazolinone ring may be any of those known in the literature discussed above. For instance, each of R and $R^1$ may, independently, be lower alkyl (preferably methyl) or halo lower alkyl such as fluoro lower alkyl (e.g. $CF_2CHF_2$ or $CHF_2$). R may also be a halogen atom such as chlorine. Preferably R is methyl and $R^1$ is $CHF_2$. The substituent X may be hydrogen; halogen such as chlorine, bromine, or fluorine (preferably fluorine); alkyl such as lower alkyl (e.g. methyl); haloalkyl such as halo lower alkyl (e.g. $CF_3$, $CH_2F$ or $CHF_2$); alkoxy such as lower alkoxy (e.g. methoxy); or nitro; and Y may be hydrogen; halogen such as chlorine, bromine, or fluorine (preferably bromine or chlorine); alkyl such as lower alkyl (e.g. methyl); alkoxy such as lower alkoxy (e.g. methoxy); haloalkyl such as halo lower alkyl (e.g. fluoroalkyl); halo lower alkylsulfinyl (e.g. —$SOCF_3$); or halo lower alkoxy (e.g. —$OCHF_2$). Presently preferred X, Y substituents are: 2-F, 4-Cl; 2-F, 4-Br; 2,4-diCl; 2-Br, 4-Cl; and 2-F, 4-$CF_3$.

In each aspect of the invention it is often preferable that any alkyl, alkenyl, alkynyl or alkylene moiety (such as the hydrocarbon moiety of an alkoxy or haloalkoxy group) have less than 6 carbon atoms, e.g. to 3 or 4 carbon atoms, and that any cycloalkyl moiety have 3 to 7 ring carbon atoms, preferably 3–6 carbon atoms.

Any acidic compound of this invention, including sulfonamides in which $NR^6R^7$ is $NHSO_2R^6$, may be converted to the corresponding base addition salt, such as a salt in which the salt-forming cation is Z (Z being as described above).

An additional aspect of the present invention pertains to the discovery that the herbicidal compounds of the invention also have fungicidal properties. Thus, use of the present compounds as herbicides give the incidental benefit of fungus disease control, prevention or moderation, particularly with respect to rice blast. Compound 5 of Table 1 is a preferred embodiment for this aspect of the invention.

Compound 5 gave 86% and 76% rice blast control at application rates of 0.125 kg/ha and 0.0313 kg/ha, respectively; rice plant injury (phytotoxicity) at the 0.125 kg/ha application rate was 27%, and at the 0.0313 kg/ha rate was 13%. The testing procedure is given below under the heading "Rice Blast Testing Procedure".

The present compounds may be prepared by methods described in the literature or in the following Examples or by methods analogous and similar thereto and within the skill of the art.

In Step A of Examples 1 and 3 below an amino compound of the formula

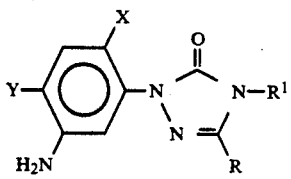

Formula III (such as the compound shown in Example 1 of International patent publication WO 87/03782, published Jul. 2, 1987) is reacted (according to the Meerwein arylation reaction or a modification thereof) with an olefinic compound having the formula $CHR^2=CR^4Q'$ to form a compound of Formula I above in which Q is $-CH(R^2)C(R^3)(R^4)Q'$ and in which $R^3$ is halogen. In this type of reaction the amino compound is converted to a diazonium salt which then reacts with the olefinic compound through a radical mechanism. The Meerwein arylation reaction is discussed in an article by Doyle et al in *J. Org. Chem.*, 42, 2431 (1977) which also describes a modification of that reaction in which an alkyl nitrite and a copper (II) halide are employed. Step A of Examples 1 and 3 employs the Doyle et al modification. Instead one may employ the unmodified reaction, in which the arenediazonium halide is initially prepared in an aqueous halogen acid solution and then mixed with the olefinic compound in the presence of an appropriate solvent (e.g. acetone) followed by the copper salt, such as copper (I) chloride.

Examples of olefinic compounds having the formula $CHR^2=CR^4Q'$ are methyl acrylate, ethyl acrylate, methyl methacrylate, methyl crotonate, methyl 3-chloroacrylate, methacrolein, vinyl methyl ketone, methacrylonitrile and acrylamide.

The product made by the reactions described above, i.e. a compound of Formula I in which Q is $-CH(R^2)C(R^3)(R^4)Q'$ and in which $R^3$ is halogen, may be treated to form other compounds of this invention. Dehydrohalogenation of that compound (e.g. with sodium hydride or other suitable base), when $R^2$ is H, yields a compound of formula II above in which Q is $-CH=C(R^4)Q'$ (as in Example 1B). That compound may be hydrogenated or halogenated to form a compound in which Q is $-CH(R^2)C(R^3)(R^4)Q'$ and $R^3$ is H (from hydrogenation, as in Example 1C) or $R^2$ and $R^3$ are halogen (from halogenation as in Example 2). When Q' is $-CO_2H$ (as produced in Example 3A), acidic compound of formula I may be (as in Examples 4 and 5) converted to the corresponding amide, as by first treating with a reagent such as thionyl chloride to form the acid halide (wherein Q' is, for example, $-COCl$) and then reacting with ammonia or an amine. Alternative methods of amide formation, involving carbodiimide-mediated coupling, are illustrated in Examples 3B, 6, and 7. In Examples 3B and 6, the amide is formed from the carboxylic acid (of e.g. formula I) and the amine, in the presence of dicyclohexylcarbodiimide, 1-hydroxybenzotriazole and a base such as a tertiary amine, e.g. N,N-diisopropylethylamine or triethylamine, in a solvent such as tetrahydrofuran. In Example 7 the amide is formed from the carboxylic acid and a sulfonamide in the presence of 1,1'-carboxyldiimidazole and a strong base such as 1,8-diazabicyclo [5.4.0]undec-7-ene in a solvent.

Instead of starting with an amino compound (of, e.g., Formula III) one may start with an otherwise identical compound having a CHO group in place of the $NH_2$ group and react it with a Witting reagent (which may be a standard type of Witting reagent or a modified type such as a Wadsworth-Emmons reagent) to form a compound of Formula II. Thus, the reagent may be an alkylidene phosphorane whose alkylidene group has the formula $=C(R^4)Q'$ such as $(C_6H_5)_3P=CHCO_2R_5$ or it may be a phosphonate ylide comprising a phosphonate diester in which the group directly attached to the P atom has the formula $-CH(R^4)Q'$ such as $(C_2H_5O)_2$-$P(O)CH_2CO_2R^5$, used together with, say, NaH in known manner. $R^5$ is preferably lower alkyl such as methyl or ethyl. The compound of Formula II may be hydrogenated to produce a compound of Formula I in which $R^2$ and $R^3$ are each hydrogen, or it may be halogenated (e.g. with chlorine) to form a compound of Formula I in which $R^2$ and $R^3$ are each halogen. The latter compound may in turn be dehydrohalogenated to form a compound of Formula II in which $R^4$ is halogen and then hydrogenated to form a compound of Formula I in which $R^4$ is halogen and $R^3$ and $R^2$ are H.

An illustration of the production of a compound having a CHO group in place of the $NH_2$ group of Formula III is given in Example 8 below.

Instead of starting with a compound containing the triazolinone ring and adding thereto the Q substituent, one may start with a compound of the formula

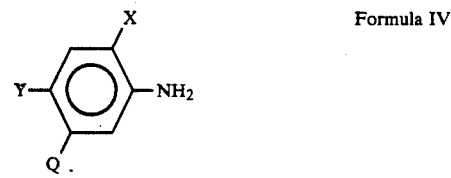

Formula IV and then form the triazolinone ring. Compounds of Formula IV are shown, for instance, in published European patent applications 300387 and 300398. The $NH_2$ group may be converted to a triazolinone ring in known manner. For instance it may be converted to an $NHNH_2$ (i.e. hydrazine) group in the conventional fashion, by diazotisation followed by reduction with sodium sulfite, and the hydrazine group may be converted to a triazolinone ring. Examples of processes for doing that are given, for instance, in U.S. Pat. No. 4,818,275, as at column 3 line 49 to column 5 line 8 of that patent; another process for converting the hydrazine group to a triazolinone ring is shown in published Japanese patent applications 60-136572 and 60-136573, published Jul. 20, 1985.

When X and Y are substituents other than H, such substituents may be introduced at various stages of the process. In Examples 1 to 8 below, such substituents are introduced prior to the formation of a compound containing the Q substituent. One or both of these substituents may be introduced after the introduction of the Q substituent; for instance, a chlorine substituent on the benzene ring may be introduced during one of the halogenation steps which modify the Q substituent, as described above.

The invention is illustrated further in the following Examples. In this application, all parts are by weight and all temperatures are in °C. unless otherwise indicated.

EXAMPLE 1

Methyl 3-[2,4-Dichloro-5-(4-Difluoromethyl-4,5-Dihydro 3-Methyl-5-Oxo-1H-1,2,4-Triazol-1-Yl)Phenyl]Propionate Step A: Methyl 2-Chloro-3-[2,4-dichloro-5-(4-difluoromethyl-4,5-dihydro-3-methyl-5-oxo-1H-1,2,4-triazol-1-yl)phenyl]propionate To a cold (0° C.), stirred mixture of 28.7 g (0.333 mole) of methyl acrylate, 2.51 g (0.0244 mole) of tertbutyl nitrite, and 2.6 g (0.019 mole) of copper (II) chloride in 50 mL of acetonitrile was added dropwise a solution of 5.0 g (0.016 mole) of 1-(5-amino-2,4-dichlorophenyl)-4-difluoromethyl-4,5-dihydro-3-methyl-1,2,4-triazol-5(1H)-one in 15 mL of acetonitrile. After complete addition the reaction mixture was allowed to warm to room temperature and was stirred for approximately 18 hours. The reaction mixture was diluted with 15 mL of 2N hydrochloric acid solution. The mixture was extracted with four portions of diethyl ether. The combined extracts were dried over anhydrous magnesium sulfate, filtered, and the filtrate evaporated under reduced pressure to give an oil. The oil was purified by column chromatography on silica gel, eluting with n-heptane:ethyl acetate (4:1) to give 5.0 g of methyl 2-chloro-3-[2,4-dichloro-5-(4-difluoromethyl-4,5-dihydro-3-methyl-5-oxo-1H-1,2,4-triazol-1-yl)phenyl]propionate as an oil, Compound 3 of Table 1.

Step B: Methyl 3-[2,4-dichloro-5-(4-difluoromethyl-4,5-dihydro-3-methyl-5-oxo-1H-1,2,4-triazol-1-yl)phenyl]-2-propenoate To a stirred, cold (0° C.) solution of 4.16 g (0.0100 mole) of methyl 2-chloro-3-[2,4-dichloro-5-(4-difluoromethyl-4,5-dihydro-3-methyl-5-oxo-1H-1,2,4-triazol-1-yl)phenyl]propionate in 15 mL of N,N-dimethylformamide was added portionwise 0.29 g (0.012 mole) of sodium hydride. After complete addition the reaction mixture was allowed to warm to room temperature and was stirred for 30 minutes. The reaction mixture was heated at 60° C. for six hours, then was stirred at room temperature for approximately 18 hours. The reaction mixture was poured into ice water, and the resultant aqueous mixture was extracted with four portions of diethyl ether. The extracts were combined and washed successively with water and an aqueous, saturated sodium chloride solution. The washed organic phase was dried over anhydrous magnesium sulfate and was filtered. The filtrate was evaporated under reduced pressure to give a white foam. The foam was purified by column chromatography on silica gel, eluting with n-heptane:ethyl acetate (4:1), to give 1.63 g of methyl 3-[2,4-dichloro-5-(4-difluoromethyl-4,5-dihydro-3-methyl-5-oxo-1H-1,2,4-triazol-1-yl)phenyl]-2-propenoate as a solid, m.p. 148°-151° C., Compound 39 of Table 1.

Step C: Methyl 3-[2,4-dichloro-5-(4-difluoromethyl-4,5-dihydro-3-methyl-5-oxo-1H-1,2,4-triazol-1-yl)phenyl]propionate Hydrogenation of 0.59 g (0.0016 mole) of methyl 3-[2,4-dichloro-5-(4-difluoromethyl-4,5-dihydro-3-methyl-5-oxo-1H-1,2,4-triazol-1-yl)phenyl]-2-propenoate (Compound 39) over approximately 0.2 g (0.0009 mole) of platinum (IV) oxide in approximately 15 mL of ethyl acetate gave 0.59 g of methyl 3-[2,4-dichloro-5-(4-difluoromethyl-4,5-dihydro-3-methyl-5-oxo-1H-1,2,4-triazol-1-yl)phenyl]propionate as a clear oil, which crystallized upon standing. The crystals were triturated with petroleum ether and recovered by filtration, m.p. 70°-73° C., Compound 1 of Table 1.

EXAMPLE 2

Methyl 2,3-Dibromo-3-[2,4-Dichloro-5-(4-Difluoromethyl-4,5-Dihydro-3-Methyl-5-Oxo-1H-1,2,4-Triazol-1-Yl)Phenyl]Propionate In a manner similar to that of Abbott and Althoresen, Org. Syn., Coll. Vol. 2, pg 270, 0.24 g (0.00063 mole) of methyl 3-[2,4-dichloro-5-(4-difluoromethyl-4,5-dihydro-3-methyl-5-oxo-1H-1,2,4-triazol-1-yl)phenyl]-2-propenoate (Compound 39) was treated with six drops of bromine in 15 mL of carbon tetrachloride to give 0.40 g of methyl 2,3-dibromo-3-[2,4-dichloro-5-(4-difluoromethyl-4,5-dihydro-3-methyl-5-oxo-1H-1,2,4-triazol-1-yl)phenyl]propionate as a solid, Compound 10 of Table 1.

The nmr spectrum was consistent with the proposed structure.

EXAMPLE 3

N-Cyclopropyl-2-Chloro-3-[2,4-Dichloro-5-(4-Difluoromethyl-4,5-Dihydro-3-Methyl-5-Oxo-1H-1,2,4-Triazol-1-yl)Phenyl]Propionamide Step A: 2-Chloro-3-[2,4-dichloro-5-(4-difluoromethyl-4,5-dihydro-3-methyl-5-oxo-1H-1,2,4-triazol-1-yl)phenyl]propionic acid To a stirred mixture of 26.3 g (0.366 mole) of acrylic acid, 2.83 g (0.275 mole) of tert-butyl nitrite, and 2.94 g (0.0220 mole) of copper (II) chloride in 75 mL of acetonitrile was added slowly 5.65 g (0.0183 mole) of 1-(5-amino-2,4-dichlorophenyl)-4-difluoromethyl-4,5-dihydro-3-methyl-1,2,4-triazol-5(1H)-one. The reaction mixture was stirred at room temperature for three hours. The reaction mixture was poured into 2N hydrochloric acid solution, and the whole was extracted with diethyl ether. The organic phase was dried over anhydrous magnesium sulfate, filtered, and the filtrate evaporated under reduced pressure to give a yellow solid. The solid was triturated with water and was filtered. The filter cake was dried to give 5.9 g of 2-chloro-3-[2,4-dichloro-5-(4-difluoromethyl-4,5-dihydro-3-methyl-5-oxo-1H-1,2,4-triazol-2-yl)phenyl]propionic acid, Compound 2 of Table 1.

The nmr spectrum was consistent with the proposed structure. A similarly prepared sample of Compound 2 had a melting point of 138°-141° C.

Step B: N-Cyclopropyl-2-chloro-3-[2,4-dichloro-5-(4-difluoromethyl-4,5-dihydro-3-methyl-5-oxo-1H-1,2,4-triazol-1-yl)phenyl]propionamide A stirred solution of 0.50 g (0.0013 mole) of 2-chloro-3-[2,4-dichloro-5-(4-difluoromethyl-4,5-dihydro-3-methyl-5-oxo-1H-1,2,4-triazol-1-yl)phenyl]propionic acid. (Compound 2), 0.071 g (0.0013 mole) of cyclopropylamine, 0.17 g (0.0013 mole) of 1-hydroxybenzotriazole hydrate, and 0.18 g (0.0014 mole) of N,N-diisopropylethylamine in approximately 15 mL of tetrahydrofuran was cooled to 0° C. To this cold mixture was added 0.26 g (0.0013 mole) of 1,3-dicyclohexylcarbodiimide. After complete addition, the reaction mixture was allowed to warm to room temperature and was stirred for approximately 18 hours. The reaction mixture was filtered. The filtrate was diluted with carbon tetrachloride and was washed in succession with a 1N hydrochloric acid solution, an aqueous 10% sodium hydroxide solution, water, and an aqueous saturated sodium chloride solution. The organic phase was dried over anhydrous magnesium sulfate, filtered, and the filtrate was evaporated under reduced pressure to give 0.43 g of N-cyclopropyl-2-chloro-3-[2,4-dichloro-5-(4-difluoromethyl-4,5-dihydro-3-methyl-5-oxo-1H-1,2,4-triazol-1-yl)phenyl]propionamide as a solid, m.p. 139°–143° C., Compound 17 of Table 1.

The nmr and ir spectra were consistent with the proposed structure.

EXAMPLE 4

N-Methyl-N-Methoxy-2-Chloro-3-[2,4-Dichloro-5-(4-Difluoromethyl-4,5-Dihydro-3-Methyl-5-Oxo-1H-1,2,4-Triazol-1-yl)Phenyl]Propionamide A mixture of 0.50 g (0.0013 mole) of 2-chloro-3-[2,4-dichloro-5-(4-difluoromethyl-4,5-dihydro-3-methyl-5-oxo-1H-1,2,4-triazol-1-yl)phenyl]propionic acid (Compound 2) and 5 mL of thionyl chloride was stirred at reflux for three hours. The mixture was cooled, and excess thionyl chloride was removed by distillation under reduced pressure leaving a residue. The residue was added to a cold solution of 0.13 g (0.0014 mole) of N,O-dimethylhydroxylamine hydrochloride and 0.11 g (0.0014 mole) of pyridine in 20 mL of tetrahydrofuran. The resultant mixture was stirred at room temperature for approximately 18 hours. The reaction mixture was diluted with diethyl ether and was washed in succession with a 1N hydrochloric acid solution, an aqueous 10% sodium hydroxide solution, water, and an aqueous saturated sodium chloride solution. The washed organic phase was dried over anhydrous magnesium sulfate and was filtered. The filtrate was evaporated under reduced pressure to give 0.37 g of N-methyl-N-methoxy-2-chloro-3-[2,4-dichloro-5-(4-difluoromethyl-4,5-dihydro-3-methyl-5-oxo-1H-1,2,4-triazol-1-yl)phenyl]propionamide as an oil, Compound 22 of Table 1.

The nmr and ir spectra were consistent with the proposed structure.

EXAMPLE 5

N-Methylsulfonyl-2-Chloro-3-[2,4-Dichloro-5-(4-Difluoromethyl-4,5-Dihydro-3-Methyl-5-Oxo-1H-1,2,4-Triazol-1-yl)Phenyl]Propionamide In a manner similar to Example 4, the reaction of 0.50 g (0.0013 mole) of 2-chloro-3-[2,4-dichloro-5-(4-difluoromethyl-4,5-dihydro-3-methyl-5-oxo-1H-1,2,4-triazol-1-yl)phenyl]propionic acid (compound 2) with 5 mL of thionyl chloride produced a residue. To this residue was added 0.50 g (0.0052 mole) of methanesulfonamide. The mixture was stirred and heated at 120° C. for two hours. The mixture was cooled, diluted with methylene chloride, and a resultant precipitate was removed by filtration. The filtrate was washed with water. The organic phase was dried over anhydrous magnesium sulfate, filtered, and the filtrate evaporated under reduced pressure to give 0.21 g of N-methylsulfonyl-2-chloro-3-[2,4-dichloro-5-(4-difluoromethyl-4,5-dihydro-3-methyl-5-oxo-1H-1,2,4-triazol-1-yl)phenyl]propionamide as a foam, Compound 25 of Table 1.

The nmr and ir spectra were consistent with the proposed structure.

EXAMPLE 6

2-Chloro-3-[2,4-Dichloro-5-(4-Difluoromethyl)-4,5-Dihydro-3-Methyl-5-Oxo-1H-1,2,4-Triazol-1-yl)Phenyl]-N-(4-Chlorophenyl)Propionamide A stirred solution of 0.50 g (0.0013 mole) of 2-chloro-3-[2,4-dichloro-5-(4-difluoromethyl-4,5-dihydro-3-methyl-5-oxo-1H-1,2,4-triazol-1-yl)phenyl]propionic acid (Compound 2), 0.16 g (0.0013 mole) of 4-chloroaniline, 0.17 g (0.0013 mole) of 1-hydroxybenzotriazole hydrate, and 0.18 g (0.0014 mole) of N,N-diisopropylethylamine in approximately 15 mL of tetrahydrofuran was cooled to 0° C. To this cold reaction mixture was added 0.26 g (0.0013 mole) of 1,3-dicyclohexylcarbodiimide. After complete addition, the reaction mixture was allowed to warm to room temperature and was stirred for approximately 18 hours. The reaction mixture was filtered. The filtrate was diluted with carbon tetrachloride and was washed in succession with a 1N hydrochloric acid solution, an aqueous 10% sodium hydroxide solution, water, and an aqueous saturated sodium chloride solution. The organic phase was dried over anhydrous magnesium sulfate, filtered, and the filtrate evaporated under reduced pressure to give 0.28 g of 2-chloro-3-[2,4-dichloro-5-(4-difluoromethyl)-4,5-dihydro-3-methyl-5-oxo-1H-1,2,4-triazol-1-yl)phenyl]-N-(4-chlorophenyl)propionamide as an oil, Compound 23 of Table 1.

The nmr and ir spectra were consistent with the proposed structure.

EXAMPLE 7

2-Chloro-3-[2-Chloro-4-Fluoro-5-(4-Difluoromethyl-4,5-Dihydro-3-Methyl-5-Oxo-1H-1,2,4-Trizol-1-yl)Phenyl]-N-(4-Methylphenylsulfonyl)Propionamide To a stirred solution of 0.19 g (0.0012 mole) of 1,1'-carbonyldiimidazole in 3 mL of tetrahydrofuran was added a solution of 0.45 g (0.0012 mole) of 2-chloro-3-[2-chloro-4-fluoro-5-(4-difluoromethyl-4,5-dihydro-3-methyl-5-oxo-1H-1,2,4-triazol-1-yl)phenyl]propionic acid (prepared by the method of Example 3, Step A, from 1-(5-amino-4-chloro-2-fluorophenyl)-4-difluoromethyl-4,5-dihydro-3-methyl-1,2,4-triazol-5(1H)-one) in 5 mL of tetrahydrofuran.

The reaction mixture was diluted with 5 mL of tetrahydrofuran. The mixture was stirred at room temperatures for 30 minutes, then was heated at reflux for 30 minutes. The reaction mixture was cooled to room temperature, and 0.20 g (0.0012 mole) of paratoluenesulfonamide was added. The mixture was stirred for approximately 10 minutes, and 0.17 g (0.0012 mole) of 1,8-diazabicyclo [5.4.0]undec-7-ene was added. The resultant mixture was stirred at room temperature for approximately 18 hours. The reaction mixture was partitioned between diethyl ether and 1N hydrochloric acid solution. The organic phase was washed in succession with water and an aqueous saturated sodium chloride solution. The washed organic phase was dried over anhydrous magnesium sulfate, filtered, and the filtrate evaporated under reduced pressure leaving a residue. This residue was purified by column chromatography on silica gel, eluting with n-heptane:ethanol:chloroform (1:1:1), to yield 0.23 g of 2-chloro-3-[2-chloro-4-fluoro-5-(4-difluoromethyl)-4,5-dihydro-3-methyl-5-oxo-1H-1,2,4-triazol-1-yl)phenyl]-N-(4-methylphenylsulfonyl)-propionamide as a solid, m.p. 267°–269° C., Compound 38 of Table 1.

The nmr spectrum was consistent with the proposed structure.

EXAMPLE 8

Ethyl 3-[2,-Chloro-4-Fluoro-5-(4-Difluoromethyl-4,5-Dihydro-3-Methyl-5-Oxo-1H-1,2,4-Triazol-1-yl)Phenyl]-Propenoate Step A: 2-(2-Chloro-4-fluoro-5-nitrophenyl)-1,3-dithiane To a solution of 53.2 g (0.261 mole) of 2-chloro-4-fluoro-5-nitrobenzaldehyde in 800 mL of methylene chloride was added 42.2 g (0.390 mole) of 1,3-propanedithiol. Boron trifluoride etherate (6.4 mL, 0.052 mole) was added to the mixture. The resulting mixture was stirred under a dry nitrogen atmosphere at room temperature for approximately 48 hours. Additional boron trifluoride etherate and 1,3-propanedithiol were added since analysis of the reaction mixture by thin layer chromatography indicated 2-chloro-4-fluoro-5-nitrobenzaldehyde was still present. The resultant mixture was stirred for an additional five hours. The reaction mixture was diluted with 300 mL of an aqueous, 5% sodium hydroxide solution. The organic phase was dried over anhydrous magnesium sulfate and was filtered. The filtrate was evaporated under reduced pressure leaving a solid residue. This solid was dissolved in a mixture of methylene chloride and n-heptane from which a solid was allowed to crystallize. This solid was removed by filtration, and the filtrate was evaporated under reduced pressure leaving 56.9 g of a solid. Analysis of this solid by nmr spectroscopy indicated that it consisted of 90% 2-(2-chloro-4-fluoro-5-nitrophenyl)-1,3-dithiane and 10% 1,3-propanedithiol.

Step B: 2-(5-Amino-2-chloro-4-fluorophenyl)-1,3-dithiane

To a stirred mixture of 20.0 g (0.0681 mole) of 2-(2-chloro-4-fluoro-5-nitrophenyl)-1,3-dithiane in 150 mL of acetic acid was added 75 mL of tetrahydrofuran. Iron powder (15.8 g, 0.269 mole) was added portionwise. Upon complete addition, the reaction mixture was heated to about 50° C. for approximately 30 minutes. The reaction mixture was cooled in an ice bath and was diluted with diethyl ether. The resultant mixture was filtered through a pad of Celite ® filter aid. Water was added to the filtrate, and the organic phase was removed. An aqueous, sodium bicarbonate solution was added to the organic phase with vigorous stirring until the mixture was slightly basic. The aqueous phase was allowed to separate from the organic phase and was removed. The aqueous phase was extracted with diethyl ether, and the extracts were added to the organic phase. This organic solution was dried over anhydrous magnesium sulfate and was filtered. The filtrate was evaporated under reduced pressure to yield 13.5 g of 2-(5-amino-2-chloro-4-fluorophenyl)-1,3-dithiane as a solid, m.p. 112°-115° C.

The nmr spectrum was consistent with the proposed structure.

Step C: Acetaldehyde 4-chloro-2-fluoro-5-(1,3-dithian-2-yl)phenylhydrazone

To a stirred, cold (−5° C.) mixture of 10.0 g (0.0379 mole) of 2-(5-amino-2-chloro-4-fluorophenyl)-1,3-dithiane in 100 mL of concentrated hydrochloric acid is added dropwise a solution of 2.55 g (0.0379 mole) of sodium nitrite in 20 mL of water. This mixture is stirred at −5° C. for approximately 45 minutes. A solution of 17.1 g (0.0758 mole) of tin (II) chloride dihydrate in 30 mL of concentrated hydrochloric acid is added dropwise. This mixture is allowed to stir for one hour. A solution of 5.16 g (0.117 mole) of acetaldehyde in 200 mL of water is added slowly. The resultant mixture is stirred for one hour during which a precipitate forms. This solid is collected by filtration and is washed with water and dried to yield acetaldehyde 4-chloro-2-fluoro-5-(1,3-dithian-2-yl)phenylhydrazone.

Step D: 1-[4-Chloro-2-fluoro-5-(1, 3-dithian-2-yl)phenyl]-4,5-dihydro-3-methyl-1,2,4-triazol-5(1H)-one To a stirred mixture of 5.00 g (0.0145 mole) of acetaldehyde 4-chloro-2-fluoro-5-(1,3-dithian-2-yl)phenylhydrazone in 50 mL of acetic acid is added dropwise a solution of 1.38 g (0.017 mole) of potassium cyanate in 5 mL of water. This mixture is stirred at 15° C. for approximately 1.5 hour. Additional aqueous potassium cyanate solution may be added if analysis of the reaction mixture by thin layer chromatography indicates the presence of acetaldehyde 4-chloro-2-fluoro-5-(1,3-dithian-2-yl)phenylhydrazone. While maintaining a temperature of 15° C., 30 mL of an aqueous, 5% sodium hypochlorite solution is added. This mixture is stirred at 15° C. for approximately one hour. The solvents are removed by distillation under reduced pressure to leave a residue. This residue is dissolved in ethyl acetate and is washed in succession with an aqueous, saturated sodium bicarbonate solution, water, and an aqueous, saturated sodium chloride solution. The washed organic solution is dried over anhydrous magnesium sulfate and is filtered. The filtrate is evaporated under reduced pressure to yield 1-[4-chloro-2-fluoro-5-(1,3-dithian-2-yl)phenyl]-4,5-dihydro-3-methyl-1,2,4-triazol-5(1H)-one.

Step E: 1-[4-Chloro-2-fluoro-5-(1,3-dithian-2-yl)phenyl]-4-difluoromethyl-4,5-dihydro-3-methyl-1,2,4-triazol-5(1H)-one A stirred mixture of 2.5 g (0.0072 mole) of 1-[4-chloro-2-fluoro-5-(1,3-dithian-2-yl)phenyl]-4,5-dihydro-3-methyl-1,2,4-triazol-5(1H)-one and 3.0 g (0.022 mole) of anhydrous potassium carbonate in 30 mL of anhydrous N,N-dimethylformamide is heated at 90° C. under a dry nitrogen atmosphere. Chlorodifluoromethane gas is bubbled into the mixture until a reflux of the gas is seen in a dry ice/acetone condenser which is fitted on the reaction flask. After approximately one hour, the reaction mixture is allowed to cool and is poured into about 300 mL of cold water forming a precipitate. This solid is collected by filtration, washed with water, and is dried to yield 1-[4-chloro-2-fluoro-5-(1,3-dithian-2-yl)phenyl]-4-difluoromethyl-4,5-dihydro-3-methyl-1,2,4-triazol-5(1H)-one.

Step F: 1-[4-Chloro-2-fluoro-5-formylphenyl)-4-difluoromethyl-4,5-dihydro-3-methyl-1,2,4-triazol-5(1H)-one A mixture of 2.0 g (0.0051 mole) of 1-[4-chloro-2-fluoro-5-(1,3-dithian-2-yl)phenyl]-4-difluoromethyl-4,5-dihydro-3-methyl-1,2,4-triazol-5(1H)-one in 25 mL of acetone and 25 mL of acetonitrile is added slowly to a stirred, cold (0° C.) solution of 5.5 g (0.031 mole) of N-bromosuccinimide in 80 mL of acetonitrile and 20 mL of water. The reaction mixture is stirred at 0° C. for about one hour. Approximately 15 mL of an aqueous, saturated sodium bisulfite solution is added. A mixture of 25 mL of methylene chloride and 25 mL of n-heptane is added, and the mixture is shaken in a separatory funnel. The organic phase is removed and is washed in succession with an aqueous, saturated sodium bicarbonate solution, water, and an aqueous, saturated sodium chloride solution. The washed organic phase is dried over anhydrous magnesium sulfate and is filtered. The filtrate is evaporated under reduced pressure to leave a residue. This residue is purified by column chromatography on silica gel to yield 1-(4-chloro-2-fluoro-5-formylphenyl)-4-difluoromethyl-4,5-dihydro-3-methyl-1,2,4-triazol-5(1H)-one.

Step G: Ethyl 3-[2-chloro-4-fluoro-5-(4-difluoromethyl-4,5-dihydro-3-methyl-5-oxo-1H-1,2,4-triazol-1-yl)phenyl]propenoate To a stirred solution of 1.0 g (0.0034 mole) of 1-(4-chloro-2-fluoro-5-formylphenyl)-4-difluoromethyl-4,5-dihydro-3-methyl-1,2,4-triazol-5(1H)-one in 15 mL of toluene is added 1.2 g (0.0034 mole) of (carbethoxymethylene)triphenylphosphorane. The reaction mixture is stirred at room temperature for about three hours and then is heated at reflux for about five hours. The reaction mixture is cooled and is diluted with diethyl ether. This mixture is washed in succession with water, 1N hydrochloric acid, an aqueous, saturated sodium bicarbonate solution, and an aqueous, saturated sodium chloride solution. The washed organic phase is dried over anhydrous magnesium sulfate and is filtered. The filtrate is evaporated under reduced pressure to leave a residue. This residue is purified by column chromatography on silica gel to yield ethyl 3-[2-chloro-4-fluoro-5-(4-difluoromethyl)-4,5-dihydro-3-methyl-5-oxo-1H-1,2,4-triazol-1-yl)phenyl]propenoate.

RICE BLAST TESTING PROCEDURE

Preparation of Inoculum

Media Preparation: A mixture of 5.0 g of agar in 500 mL of water was heated until the agar melted. A mixture of 40.0 g of Quaker ® Instant Oatmeal in 250 mL of water was added. The mixture was placed in an autoclave and was heated at 121° C. for 0.5 hour. After cooling, approximately 50 mL of the media was poured into each of 15 petri dishes.

Inoculum Preparation: Under sterile conditions, each petri dish was inoculated with mycelial plugs of *Pyricularia oryzae* (race IB-49) onto the surface of the media. The inoculated plates were incubated for seven to ten days in a growth chamber at 25° C., approximately 40% humidity, and a photo period of 12 hours of light and 12 hours of dark using fluorescent lamps. The mycelia from the incubated plates were scraped into a beaker, and the resulting mixture was blended. This mixture was filtered through cheesecloth, and the filtrate which contained the rice blast spores was saved for the inoculation of rice plants.

Rice Treatment

Plastic pots (7 cm × 7 cm × 6.5 cm) were filled to an approximate depth of 4.5 cm with steam-sterilized sandy loam soil. The soil was leveled and pressed with a flat templet. Approximately 10 to 15 seeds of rice were placed on the flattened soil, and the seeds were firmly pressed into soil. A topping soil of equal proportions of sand and sandy loam soil was placed uniformly on top of each flat to a depth of approximately 0.5 cm.

The pots were placed in a greenhouse and watered regularly for 14 days after which the pots were drenched with a solution of the test compound as described below. One day post treatment the rice plants were inoculated with the rice blast spore suspension using a DeVilbiss hand held sprayer. The inoculated plants were immediately placed in a dark, humidified growth chamber (72° F., 88% humidity) for 24 hours. The flats were moved to a greenhouse and were bottom watered for the duration of the test.

The test compounds were applied as 50 g/liter flowable or an emulsifiable concentrate at rates equivalent to 0.125 kg/ha or submultiples thereof, i.e., 0.0313 kg/ha, 0.0078 kg/ha, and so on. The applications were made as soil drenches using 20 mL of test solution of the appropriate concentration for each of three pots per compound.

For pots the size described above, an application rate of 0.125 kg/ha of test compound is equivalent to 0.000079 g/pot. A solution of 0.000435 g of test compound in 120 mL of distilled water containing 0.5% v/v of sorbitan monolaurate emulsifier/solubilizer was prepared. For application as a soil drench to the test pots, 60 mL of this solution was divided equally between the three pots (i.e. 20 mL per pot). The remaining 60 mL of the 0.125 kg/ha solution was decanted into 60 mL of the distilled water/emulsifier solution to produce a 120 mL solution containing 0.000217 g of the test compound, a rate of 0.0625 kg/ha. Sixty mL of this solution was decanted into 60 mL of the water/emulsifier solution to produce 120 mL of a mixture which contained 0.000108 g of the test compound, a rate of 0.0313 kg/ha. The process above was repeated, i.e. 60 mL of the 0.0313 kg/ha solution was used for the soil drench application and 60 mL was decanted into 60 mL of water/emulsifier solution for the 0.0156 kg/ha rate, etc.

The rice plant injury (phytotoxicity) and fungicidal activity were recorded at seven days post treatment. Phytotoxicity data were taken as percent control.

HERBICIDAL ACTIVITY

The plant test species used in demonstrating the herbicidal activity of compounds of this invention include cotton (*Gossypium hirsutum* var. DPLGI), soybean (*Glycine max* var. Williams), field corn (*Zea mays* var. Pioneer 3732), wheat (*Triticum aestivium* var. Wheaton), rice (*Oryza sativa* var. Labelle), morningglory (*Ipomea lacumosa* or *Ipomea hederacea*), wild mustard (*Brassica kaber*), velvetleaf (*Abutilon theophrasti*), barnyardgrass (*Echinochloa crus-galli*), green foxtail (*Setaria viridis*), and johnsongrass (*Sorghum halepense*).

Preparation of Flats

Preemergence

Two disposable fiber flats (8 cm × 15 cm × 25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below.

Postemergence

Two flats for each rate of application for each herbicide candidate are also prepared for postemergence application. The postemergence flats are prepared in the same manner as discussed above for the preemergence flats. The prepared flats are watered for 8-11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24 g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | 172stroyed, Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in Tables 3 and 4 below. The test compounds are identified in the tables by numbers which correspond to those in Table 1. The abbreviation "kg/ha" in Tables 3 and 4 means kilograms per hectare.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfonated aliphatic polyester as wetting agents. Other wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
|---|---|
| Active ingredient | 53.01 |

-continued

| Component: | % by Wt. |
|---|---|
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
|---|---|
| Oil Suspension: | |
| Active ingredient | 25.00 |
| Polyoxyethylene sorbitol hexaoleate | 5.00 |
| Highly aliphatic hydrocarbon oil | 70.00 |
| Total | 100.00 |
| Aqueous Suspension: | |

-continued

|  | % by Wt. |
|---|---|
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; for example, with Compound 5 (Table 1) applied postemergently, amounts as low as 7 g/ha or less, e.g. 7-125 g/ha, may be employed for control of broad leafed weeds (e.g. cocklebur, velvetleaf, morningglory, or nightshade) with little or no injury to crops such as maize. For field use, where there are losses of herbicide, higher application rates (e.g. four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatylethyl); benzothiadiazinone herbicides such as 3-(1-methylethyl)-(1H)-2,1,3-benzothiadiazin-4-(3H)-one,2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methyl-propanenitrile (cyanazine); dinitroaniline herbicides such as 2,6-dinitro-N,N-dipropyl-4-(trifluoromethyl)-benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

Among the other herbicides that may be used in combination with the herbicides of this invention are, in one preferred embodiment, two which have been found to provide unexpected synergistic effects when used with certain of the instantly claimed compounds. More particularly it has been found that when the herbicide monoammonium 2-amino-4-[(hydroxy)methylphosphinyl]-butanoate sold under the trade name Ignite ® by Hoechst-Roussel Agri-Vet Co., Somerville, N.J., or the sodium salt of L-2-amino-4-[(hydroxy)(methyl)-phosphinyl]-butyryl-L-alanyl-L-alanine (bialaplhos) available from Meiji Seika under the trade name Herbiace ®, is used with at least one of the claimed compounds of the formula

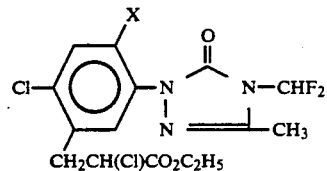

where x is chlorine or fluorine, i.e. Compounds 4 and of Table 1 (below) respectively, there is obtained a marked increase in the activity of the combination against a number of weed species as contrasted with the results of either compound alone, as shown by Examples 9 and 10 below. Conversely, it will be seen that reduced amounts of the herbicides to achieve the same effect can also be achieved, resulting in economic savings and reducing the amount of herbicide used per acre.

The weight ratio of the herbicides of this invention to these latter two commercial herbicides (above) is not critical, and may range from about 1:25 to 1:1, more preferably 1:20 to 1:5, where the total weight of the combination in a given formulation may be in the same amounts as those shown above for any claimed compound alone.

EXAMPLE 9

The Combination of Ethyl 2-Chloro-3-[2-chloro-4-fluoro-5-(4-difluoromethyl-4,5-dihydro-3-methyl-5-oxo-1H-1,2,4-triazol-1-yl)phenyl]-propionate (Test Compound A) and Monoammonium 2-Amino-4-[(hydroxy)methylphosphinyl]-butanoate (Test Compound B), Providing Increased Herbicidal Activity Test plots in the following locations were planted with twenty-six weed species to determine the herbicidal activity of the test compounds: Cali, Columbia (CJM); Sparks, Ga. (SRS); and Champaign, Ill. (CRS). The test compounds were applied postemergence at rates of: 0.015; 0.031; and 0.063 pounds per acre—Test Compound A; 0.3 and 1.0 pound per acre—Test Compound B; and in combination at 0.015/0.3; 0.031/0.3; and 0.063/0.3 pound per acre—Test Compound A/Test Compound B. The test compounds were applied as aqueous mixtures sprayed onto the foliage of the test species at 15 days after planting (SRS); 18 days after planting (CJM); and 49 days after planting (CRS). Four test plots were treated for each rate. A spray adjuvant, Ortho X-77®, was added to each tank mix of formulated test compound and water at the rate of 0.25% volume/volume. (Ortho X-77-a quick wetting agent (Chevron Chemical Co., California).

Test compound A was formulated as a 0.417 pound per gallon emulsifiable concentrate using the following formula:

| | % (wt/wt) |
|---|---|
| Test Compound A | 5.89 |
| Anionic calcium salt of dodecylbenzene sulfonate[a] | 4.06 |
| Nonionic 6-molar ethylene oxide condensation product of nonylphenol[b] | 0.33 |
| Nonionic 30-molar ethylene oxide condensation product of nonylphenol[c] | 1.14 |
| Nonionic paste of 100% polyalkylene glycol ether[d] | 0.97 |
| Refined xylene - diluent | 87.61 |
| | 100.00 |

(a), (b), (c), and (d) are emulsifiers for herbicide formulations.

In order to obtain the above 0.015 lb/acre rate of application, 136.3 ml of the 0.417 lb/gal formulation was employed per acre. The 0.031 and 0.063 lb/acre formulations were similarly prepared on a proportional basis.

Test Compound B (known as Ignite® herbicide) is an already-formulated commercial 1.67 pound per gallon aqueous solution produced by Hoechst-Roussel Agri-Vet Company, Somerville, N.J.

In order to obtain the above 0.3 lb/acre rate of application, 680.8 ml of the 1.67 lb/gal formulation was employed per acre. The 1.0 lb/acre formulation was similarly prepared on a proportional basis.

The combination of Test Compounds A and B, as stated above, was formulated by mixing the above 0.015; 0.031; and 0.063 lb/acre formulations respectively of Compound A with the 0.3 lb/acre formulation of Compound B, to form the three Test Compound A/Test Compound B formulations. Thus, for example, 281.8 ml of formulated Compound A was mixed with 680 ml of formulated Compound B in a weight ratio of 1:10 to form a 0.0166 lb. per gallon per acre solution.

Upon determination of the proper amounts of the formulated materials needed for the various rates of application, those amounts of the formulation of Compound A and/or Compound B were placed in a spray tank with 0.5 gallon of Ortho X-77® spray adjuvant (0.25% v/v). The mixture was diluted to 20 gallons with water to provide sufficient spray for treatment of 1 acre at the rate of application calculated.

The herbicidal data from these tests are summarized below in Table 5 (Test Compound A alone); Table 6 (Test Compound B alone); and Table 7 (The combination of Test Compounds A and B).

When used in combination at the rates of 0.031 pounds per acre—A and 0.3 pound per acre—B, a significant increase in herbicidal activity is seen in a number of weed species. These species are: hairy beggarticks, Florida beggarweed, wild poinsettia, morningglory, prickly sida, southern sandbur, large crabgrass, goosegrass, green foxtail, and Johnsongrass. These results appear to be separate from the effects of the test compounds alone, i.e., the species controlled by test Compound A alone are still controlled and those species controlled by Compound B alone are still controlled. However, the combination of A and B appear to have an extra effect in controlling weed species which neither test compound alone is able to control adequately.

In accordance with the foregoing procedures, but substituting bialaphos for the monoammonium 2-amino-4-[(hydroxy)methylphosphinyl]butanoate in the combination of Test Compound A with B, there is likewise obtained an herbicidally effective composition.

EXAMPLE 10

In accordance with the test procedures of Example 9 but substituting ethyl 2-chloro-3-[2,4-dichloro-5-(difluoromethyl-4,5-dihydro-3-methyl-5-oxo-1H-1,2,4-triazol-1-yl)phenyl]propionate for Test Compound A in combination with butanoate Test Compound B, there is also obtained an herbicidally effective composition.

In accordance with the foregoing procedure but substituting bialaphos for the monoammonium 2-amino-4-[(hydroxy)methylphosphinyl]butanoate in the combination of the 4-chlorophenyl-substituted Test Compound A with B, there is likewise obtained an herbicidally effective composition.

It is apparent that various modifications may be made in the formulations and applications of the compounds of this invention without departing from the inventive concepts herein as defined in the claims.

TABLE 1

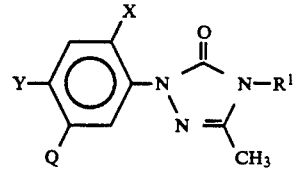

| Cmpd No. | X | Y | Q | $R^1$ |
|---|---|---|---|---|
| 1 | Cl | Cl | $CH_2CH_2CO_2CH_3$ | $CHF_2$ |
| 2 | Cl | Cl | $CH_2CH(Cl)CO_2H$ | $CHF_2$ |
| 3 | Cl | Cl | $CH_2CH(Cl)CO_2CH_3$ | $CHF_2$ |
| 4 | Cl | Cl | $CH_2CH(Cl)CO_2C_2H_5$ | $CHF_2$ |
| 5 | F | Cl | $CH_2CH(Cl)CO_2C_2H_5$ | $CHF_2$ |
| 6 | Cl | Cl | $CH_2CH(Br)CO_2C_2H_5$ | $CHF_2$ |
| 7 | Cl | Cl | $CH_2CH(Cl)CO_2CH(CH_3)_2$· | $CHF_2$ |
| 8 | Cl | Cl | $CH_2CH(Cl)CO_2CH(CH_3)CH_2CH_3$ | $CHF_2$ |
| 9 | Cl | Cl | $CH_2CH(Cl)CO_2CH_2C_6H_5$ | $CHF_2$ |
| 10 | Cl | Cl | $CH(Br)CH(Br)CO_2CH_3$ | $CHF_2$ |
| 11 | Cl | Cl | $CH(Br)CH(Br)CO_2C_2H_5$ | $CHF_2$ |
| 12 | Cl | Cl | $CH(CH_3)CH(Cl)CO_2C_2H_5$ | $CHF_2$ |

TABLE 1-continued

[Structure: Y-, X-, Q-substituted phenyl attached to N-N=C(CH3) ring with C(O)N-R¹]

| Cmpd No. | X | Y | Q | R¹ |
|---|---|---|---|---|
| 13 | F | Cl | CH₂C(Cl)(CH₃)CO₂CH₃ | CHF₂ |
| 14 | Cl | Cl | CH₂CH(Cl)C(O)NH₂ | CHF₂ |
| 15 | Cl | Cl | CH₂CH(Cl)C(O)NHCH₃ | CHF₂ |
| 16 | Cl | Cl | CH₂CH(Cl)C(O)N(CH₃)₂ | CHF₂ |
| 17 | Cl | Cl | CH₂CH(Cl)C(O)NH-cyclopropyl | CHF₂ |
| 18 | Cl | Cl | CH₂CH(Cl)C(O)NHCH₂CH=CH₂ | CHF₂ |
| 19 | Cl | Cl | CH₂CH(Cl)C(O)NHCH₂CN | CHF₂ |
| 20 | Cl | Cl | CH₂CH(Cl)C(O)NHOH | CHF₂ |
| 21 | Cl | Cl | CH₂CH(Cl)C(O)NHOCH₃ | CHF₂ |
| 22 | Cl | Cl | CH₂CH(Cl)C(O)N(CH₃)OCH₃ | CHF₂ |
| 23 | Cl | Cl | CH₂CH(Cl)C(O)NHC₆H₄-4-Cl | CHF₂ |
| 24 | Cl | Cl | CH₂CH(Cl)C(O)NHCH₂C₆H₄-4-Cl | CHF₂ |
| 25 | Cl | Cl | CH₂CH(Cl)C(O)NHSO₂CH₃ | CHF₂ |
| 26 | Cl | Cl | CH₂CH(Cl)C(O)NHSO₂C₆H₄-4-Cl | CHF₂ |
| 27 | Cl | Cl | CH₂CH(Cl)C(O)NHSO₂C₆H₄-4-CH₃ | CHF₂ |
| 28 | F | Cl | CH₂CH(CH₃)CO₂CH₃ | CHF₂ |
| 29 | F | Cl | CH₂CH(Cl)C(O)NH-cyclopropyl | CHF₂ |
| 30 | F | Cl | CH₂CH(Cl)C(O)NHCH₂CN | CHF₂ |
| 31 | F | Cl | CH₂CH(Cl)C(O)N(CH₃)OCH₃ | CHF₂ |
| 32 | F | Cl | CH₂CH(Cl)C(O)NHSO₂CH₃ | CHF₂ |
| 33 | F | Cl | CH₂CH(Cl)C(O)NHSO₂CF₃ | CHF₂ |
| 34 | F | Cl | CH₂CH(Cl)C(O)NHSO₂C₆H₄-2-Cl | CHF₂ |
| 35 | F | Cl | CH₂CH(Cl)C(O)NHSO₂C₆H₄-3-Cl | CHF₂ |
| 36 | F | Cl | CH₂CH(Cl)C(O)NHSO₂C₆H₄-4-Cl | CHF₂ |
| 37 | F | Cl | CH₂CH(Cl)C(O)NHSO₂CH(CH₃)₂ | CHF₂ |
| 38 | F | Cl | CH₂CH(Cl)C(O)NHSO₂C₆H₄-4-CH₃ | CHF₂ |
| 39 | Cl | Cl | CH=CHCO₂CH₃ (trans) | CHF₂ |
| 40 | Cl | Cl | CH=CHCO₂C₂H₅ (trans) | CHF₂ |
| 41 | F | Cl | CH=CHCO₂C₂H₅ (trans) | CHF₂ |
| 42 | Cl | Cl | CH=CHCO₂CH₂C₆H₅ (trans) | CHF₂ |
| 43 | F | Cl | CH=C(CH₃)CO₂CH₃ (trans) | CHF₂ |
| 44 | Cl | Cl | CH₂CH(Cl)CN | CHF₂ |
| 45 | F | Cl | CH₂CH(Cl)CO₂CH₃ | CHF₂ |
| 46 | F | Cl | CH₂CH(Cl)COOH | CHF₂ |
| 47 | Cl | Cl | CH₂CH(Cl)COCH₃ | CHF₂ |
| 48 | Cl | Cl | CH₂CH(Cl)CONHCH₂CH₂CH₃ | CHF₂ |
| 49 | Cl | Cl | CH₂CH(Cl)CONHCH₂CH₂CH₃ | CHF₂ |
| 50 | Cl | Cl | CH₂CH(Cl)CONHCH(CH₃)CH₂CH₃ | CHF₂ |
| 51 | Cl | Cl | CH₂CH(Cl)CONH-cyclopentyl | CHF₂ |
| 52 | Cl | Cl | CH=CHCONH-cyclopentyl (trans) | CHF₂ |
| 53 | Cl | Cl | CH=CHCONHCH₂CH₂CH₃ (trans) | CHF₂ |
| 54 | Cl | Cl | CH=CHCONHCH(CH₃)CH₂CH₃ (trans) | CHF₂ |
| 55 | F | Cl | CH=CHCO₂CH₃ (cis/trans mix) | CHF₂ |
| 56 | F | Cl | CH₂CH(Cl)CO₂CH(CH₃)₂ | CHF₂ |
| 57 | Cl | Cl | CH₂CH(Cl)CONHCH(CH₃)₂ | CHF₂ |
| 58 | Cl | Cl | CH=CHCONHCH(CH₃)₂ (trans) | CHF₂ |
| 59 | Cl | Cl | CH₂CH(Cl)CONHC₂H₅ | CHF₂ |
| 60 | Cl | Cl | CH=CHCONHC₂H₅ (trans) | CHF₂ |
| 61 | F | Cl | CH₂CH(Cl)CHO | CHF₂ |
| 62 | F | Cl | CH₂CH(Cl)CO₂Ca1/2* | CHF₂ |
| 63 | F | Cl | CH₂CH(Cl)CO₂K | CHF₂ |
| 64 | F | Cl | CH₂CH(Cl)CO₂NH(C₂H₅)₃ | CHF₂ |
| 65 | Cl | Cl | CH₂CH(Cl)CO₂CH₃ | CF₂CHF₂ |
| 66 | F | Cl | CH₂CH(Cl)CO₂CH₃ | CF₂CHF₂ |
| 67 | F | Cl | CH₂CH(Cl)CO₂C₂H₅ | CF₂CHF₂ |
| 68 | F | Cl | CH₂C(Cl)(CH₃)CO₂CH₃ | CF₂CHF₂ |
| 69 | Cl | Cl | CH₂CH(Cl)CO₂CH₂CO₂CH₃ | CHF₂ |
| 70 | Cl | Cl | CH₂CH(Br)CO₂CH₃ | CHF₂ |
| 71 | F | Cl | CH₂CH(Cl)CO₂Na | CHF₂ |
| 72 | Cl | Cl | CH₂CH(Cl)C(O)NHSO₂CH₂C₆H₅ | CHF₂ |
| 73 | Cl | Cl | CH=CHCO₂H (trans) | CHF₂ |
| 74 | Cl | Cl | CH=CHC(O)NH₂ (trans) | CHF₂ |

*Calcium salt containing 2 equivalents of the acid moiety.

TABLE 2

Measured Melting Points

| Cmpd No. | m.p. (°C.) |
|---|---|
| 1 | 70–73 |
| 2 | 138–141 |
| 3 | oil |
| 4 | oil |

TABLE 2-continued

Measured Melting Points

| Cmpd No. | m.p. (°C.) |
|---|---|
| 5 | oil |
| 6 | oil |
| 7 | oil |
| 8 | oil |
| 9 | oil |
| 10 | solid |
| 11 | 58-60 |
| 12 | oil |
| 13 | oil |
| 14 | 164-167 |
| 15 | foam* |
| 16 | oil |
| 17 | 139-143 |
| 18 | oil |
| 19 | 155-157 |
| 20 | foam* |
| 21 | foam* |
| 22 | oil |
| 23 | oil |
| 24 | oil |
| 25 | foam* |
| 26 | foam* |
| 27 | foam* |
| 28 | oil |
| 29 | foam* |
| 30 | 158-160 |
| 31 | 125-127 |
| 34 | foam* |
| 35 | oil |
| 36 | foam* |
| 37 | foam* |
| 38 | 267-269 dec |
| 39 | 148-151 |
| 40 | 140-141 |
| 41 | 119-122 |
| 42 | 101-105 |
| 43 | 96-98 |
| 44 | oil |
| 45 | oil |
| 46 | >280 |
| 47 | oil |
| 48 | oil |
| 49 | oil |
| 50 | oil |
| 51 | 153.5-155 |
| 52 | 162-164 |
| 53 | 74-76 |
| 54 | 85-88 |
| 55 | oily solid |
| 57 | foam* |
| 58 | 188-191 |
| 59 | 141-142 |
| 60 | 81-83 |
| 62 | >280 |
| 63 | 195 dec |
| 64 | oil |
| 65 | oil |
| 66 | oil |
| 67 | oil |
| 68 | oil |
| 69 | oil |
| 70 | oil |
| 71 | 173-174 |
| 72 | oil |
| 73 | 210-212 |
| 74 | 180-184 |

*Materials designated as "foam" were recovered as amorph solids with no definite melting point.

TABLE 3

PREEMERGENCE HERBICIDAL ACTIVITY (% CONTROL)

| | Compound No. | | |
|---|---|---|---|
| | 1 | 2 | 3 |
| | Rate (kg/ha) | | |
| Species | 0.5 | 0.5 | 0.5 |
| Cotton | 0 | 90 | 50 |
| Soybean | 0 | 0 | 5 |
| Field Corn | 30 | 10 | 10 |
| Rice | 60 | 10 | 5 |
| Wheat | 5 | 0 | 5 |
| Morningglory | 50 | 100 | 95 |
| Wild Mustard | 70 | 90 | 100 |
| Velvetleaf | 95 | 100 | 100 |
| Barnyardgrass | 30 | 5 | 70 |
| Green Foxtail | 50 | 10 | 85 |
| Johnsongrass | 50 | 30 | 50 |

| | Compound No. | | |
|---|---|---|---|
| | 4 | 5 | 6 |
| | Rate (kg/ha) | | |
| Species | 0.5 | 0.5 | 0.5 |
| Cotton | 70 | 90 | 30 |
| Soybean | 5 | 0 | 5 |
| Field Corn | 10 | 5 | 10 |
| Rice | 15 | 10 | 5 |
| Wheat | 10 | 20 | 0 |
| Morningglory | 100 | 100 | 50 |
| Wild Mustard | 100 | 100 | 60 |
| Velvetleaf | 100 | 100 | 100 |
| Barnyardgrass | 40 | 20 | 0 |
| Green Foxtail | 5 | 5 | 0 |
| Johnsongrass | 70 | 40 | 5 |

| | Compound No. | | |
|---|---|---|---|
| | 7 | 8 | 9 |
| | Rate (kg/ha) | | |
| Species | 0.5 | 0.5 | 0.5 |
| Cotton | 90 | 80 | 80 |
| Soybean | 0 | 0 | 0 |
| Field Corn | 15 | 10 | 10 |
| Rice | 15 | 5 | 30 |
| Wheat | 0 | 0 | 5 |
| Morningglory | 90 | 40 | 100 |
| Wild Mustard | 100 | 90 | 95 |
| Velvetleaf | 95 | 100 | 100 |
| Barnyardgrass | 50 | 5 | 70 |
| Green Foxtail | 50 | 10 | 30 |
| Johnsongrass | 20 | 60 | 85 |

| | Compound No. | | |
|---|---|---|---|
| | 10 | 11 | 12 |
| | Rate (kg/ha) | | |
| Species | 0.5 | 0.5 | 0.5 |
| Cotton | 5 | 10 | 50 |
| Soybean | 10 | 0 | 0 |
| Field Corn | 0 | 20 | 40 |
| Rice | 15 | 40 | 30 |
| Wheat | 0 | 5 | 60 |
| Morningglory | 30 | 50 | 100 |
| Wild Mustard | 100 | 100 | 95 |
| Velvetleaf | 100 | 100 | 100 |
| Barnyardgrass | 85 | 100 | 95 |
| Green Foxtail | 100 | 95 | 100 |
| Johnsongrass | 50 | 90 | 85 |

| | Compound No. | | |
|---|---|---|---|
| | 13 | 14 | 15 |
| | Rate (kg/ha) | | |
| Species | 0.5 | 0.5 | 0.5 |
| Cotton | 30 | 90 | 80 |
| Soybean | 0 | 95 | 95 |
| Field Corn | 10 | 95 | 95 |
| Rice | 5 | 95 | 95 |
| Wheat | 20 | 95 | 95 |
| Morningglory | 100 | 100 | 95 |
| Wild Mustard | 100 | 100 | 100 |
| Velvetleaf | 100 | 100 | 100 |
| Barnyardgrass | 60 | 100 | 95 |
| Green Foxtail | 5 | 100 | 100 |
| Johnsongrass | 30 | 100 | 100 |

| | Compound No. | | |
|---|---|---|---|
| | 16 | 17 | 18 |

TABLE 3-continued
PREEMERGENCE HERBICIDAL ACTIVITY (% CONTROL)

| | Rate (kg/ha) | | |
|---|---|---|---|
| Species | 0.5 | 0.5 | 0.5 |
| Cotton | 80 | 60 | 70 |
| Soybean | 90 | 100 | 90 |
| Field Corn | 95 | 95 | 90 |
| Rice | 95 | 90 | 90 |
| Wheat | 95 | 100 | 95 |
| Morningglory | 70 | 100 | 95 |
| Wild Mustard | 100 | 100 | 100 |
| Velvetleaf | 100 | 100 | 100 |
| Barnyardgrass | 95 | 100 | 90 |
| Green Foxtail | 100 | 100 | 100 |
| Johnsongrass | 95 | 100 | 95 |

| | Compound No. | | |
|---|---|---|---|
| | 19 | 22 | 23 |
| | Rate (kg/ha) | | |
| Species | 0.5 | 0.5 | 0.5 |
| Cotton | 20 | 40 | 15 |
| Soybean | 50 | 5 | 5 |
| Field Corn | 80 | 85 | 0 |
| Rice | 60 | 30 | 5 |
| Wheat | 95 | 90 | 0 |
| Morningglory | 100 | 95 | 15 |
| Wild Mustard | 100 | 100 | 95 |
| Velvetleaf | 100 | 100 | 100 |
| Barnyardgrass | 95 | 100 | 5 |
| Green Foxtail | 95 | 100 | 95 |
| Johnsongrass | 100 | 95 | 20 |

| | Compound No. | | |
|---|---|---|---|
| | 24 | 25 | 26 |
| | Rate (kg/ha) | | |
| Species | 0.5 | 0.5 | 0.5 |
| Cotton | 30 | 80 | 85 |
| Soybean | 10 | 5 | 5 |
| Field Corn | 5 | 80 | 50 |
| Rice | 5 | 40 | 40 |
| Wheat | 5 | 85 | 50 |
| Morningglory | 50 | 100 | 80 |
| Wild Mustard | 100 | 100 | 100 |
| Velvetleaf | 100 | 100 | 100 |
| Barnyardgrass | 70 | 70 | 15 |
| Green Foxtail | 100 | 95 | 60 |
| Johnsongrass | 50 | 80 | 50 |

| | Compound No. | | |
|---|---|---|---|
| | 27 | 28 | 29 |
| | Rate (kg/ha) | | |
| Species | 0.5 | 0.25 | 0.5 |
| Cotton | 10 | 0 | 100 |
| Soybean | 5 | 0 | 100 |
| Field Corn | 70 | 5 | 100 |
| Rice | 40 | 5 | 100 |
| Wheat | 70 | 15 | 100 |
| Morningglory | 85 | 20 | 100 |
| Wild Mustard | 100 | 50 | 100 |
| Velvetleaf | 100 | 100 | 100 |
| Barnyardgrass | 80 | 40 | 100 |
| Green Foxtail | 95 | 0 | 100 |
| Johnsongrass | 70 | 20 | 100 |

| | Compound No. | | |
|---|---|---|---|
| | 30 | 31 | 33 |
| | Rate (kg/ha) | | |
| Species | 0.25 | 0.5 | 0.25 |
| Cotton | 80 | 70 | 10 |
| Soybean | 80 | 100 | 0 |
| Field Corn | 85 | 95 | 15 |
| Rice | 95 | 85 | 0 |
| Wheat | 95 | 95 | 5 |
| Morningglory | 100 | 100 | 85 |
| Wild Mustard | 100 | 100 | 90 |
| Velvetleaf | 100 | 100 | 95 |
| Barnyardgrass | 80 | 100 | 5 |
| Green Foxtail | 100 | 100 | 5 |
| Johnsongrass | 85 | 95 | 15 |

| | Compound No. | | |
|---|---|---|---|
| | 34 | 36 | 37 |
| | Rate (kg/ha) | | |
| Species | 0.25 | 0.25 | 0.25 |
| Cotton | 95 | 30 | 70 |
| Soybean | 0 | 0 | 5 |
| Field Corn | 5 | 15 | 30 |
| Rice | 5 | 5 | 40 |
| Wheat | 5 | 10 | 15 |
| Morningglory | 100 | 100 | 100 |
| Wild Mustard | 95 | 100 | 100 |
| Velvetleaf | 100 | 100 | 100 |
| Barnyardgrass | 5 | 90 | 30 |
| Green Foxtail | 0 | 85 | 0 |
| Johnsongrass | 10 | 10 | 30 |

| | Compound No. | | |
|---|---|---|---|
| | 39 | 40 | 41 |
| | Rate (kg/ha) | | |
| Species | 0.5 | 0.5 | 0.5 |
| Cotton | 30 | 10 | 20 |
| Soybean | 10 | 15 | 0 |
| Field Corn | 30 | 30 | 10 |
| Rice | 60 | 40 | 10 |
| Wheat | 10 | 5 | 30 |
| Morningglory | 5 | 20 | 95 |
| Wild Mustard | 95 | 100 | 100 |
| Velvetleaf | 95 | 100 | 100 |
| Barnyardgrass | 80 | 90 | 10 |
| Green Foxtail | 100 | 100 | 70 |
| Johnsongrass | 95 | 30 | 20 |

| | Compound No. | | |
|---|---|---|---|
| | 42 | 43 | 48 |
| | Rate (kg/ha) | | |
| Species | 0.5 | 0.5 | 0.25 |
| Cotton | 90 | 5 | 20 |
| Soybean | 5 | 5 | 70 |
| Field Corn | 5 | 10 | 80 |
| Rice | 15 | 10 | 40 |
| Wheat | 5 | 10 | 80 |
| Morningglory | 20 | 80 | 50 |
| Wild Mustard | 80 | 100 | 100 |
| Velvetleaf | 10 | 100 | 100 |
| Barnyardgrass | 20 | 50 | 95 |
| Green Foxtail | 50 | 100 | 100 |
| Johnsongrass | 20 | 40 | 95 |

| | Compound No. | | |
|---|---|---|---|
| | 49 | 50 | 51 |
| | Rate (kg/ha) | | |
| Species | 0.25 | 0.25 | 0.25 |
| Cotton | 15 | 10 | 20 |
| Soybean | 20 | 50 | 30 |
| Field Corn | 40 | 70 | 80 |
| Rice | 15 | 10 | 15 |
| Wheat | 20 | 50 | 40 |
| Morningglory | 20 | 70 | 60 |
| Wild Mustard | 50 | 100 | 80 |
| Velvetleaf | 100 | 100 | 100 |
| Barnyardgrass | 85 | 95 | 95 |
| Green Foxtail | 100 | 100 | 100 |
| Johnsongrass | 70 | 80 | 95 |

| | Compound No. | | |
|---|---|---|---|
| | 52 | 53 | 54 |
| | Rate (kg/ha) | | |
| Species | 0.25 | 0.25 | 0.25 |
| Cotton | 20 | 40 | 15 |
| Soybean | 10 | 10 | 40 |
| Field Corn | 30 | 30 | 20 |
| Rice | 0 | 5 | 5 |
| Wheat | 5 | 10 | 20 |
| Morningglory | 30 | 30 | 60 |
| Wild Mustard | 100 | 95 | 100 |
| Velvetleaf | 100 | 100 | 100 |
| Barnyardgrass | 5 | 15 | 20 |

TABLE 3-continued

PREEMERGENCE HERBICIDAL ACTIVITY (% CONTROL)

| | | | |
|---|---|---|---|
| Green Foxtail | 80 | 95 | 95 |
| Johnsongrass | 15 | 60 | 70 |

| | Compound No. | | |
|---|---|---|---|
| | 57 | 58 | 59 |
| | Rate (kg/ha) | | |
| Species | 0.25 | 0.25 | 0.25 |
| Cotton | 80 | 15 | 70 |
| Soybean | 90 | 80 | 90 |
| Field Corn | 95 | 50 | 90 |
| Rice | 70 | 60 | 90 |
| Wheat | 95 | 70 | 90 |
| Morningglory | 80 | 70 | 85 |
| Wild Mustard | 100 | 100 | 100 |
| Velvetleaf | 100 | 100 | 100 |
| Barnyardgrass | 95 | 40 | 100 |
| Green Foxtail | 100 | 100 | 100 |
| Johnsongrass | 95 | 70 | 100 |

| | Compound No. | | |
|---|---|---|---|
| | 60 | 62 | 63 |
| | Rate (kg/ha) | | |
| Species | 0.25 | 0.125 | 0.125 |
| Cotton | 5 | 80 | 50 |
| Soybean | 15 | 0 | 30 |
| Field Corn | 30 | 0 | 0 |
| Rice | 50 | 30 | 50 |
| Wheat | 30 | 5 | 5 |
| Morningglory | 50 | 100 | 90 |
| Wild Mustard | 60 | 100 | 100 |
| Velvetleaf | 100 | 100 | 100 |
| Barnyardgrass | 80 | 70 | 50 |
| Green Foxtail | 100 | 40 | 80 |
| Johnsongrass | 95 | 30 | 30 |

| | Compound No. | | |
|---|---|---|---|
| | 64 | 65 | 66 |
| | Rate (kg/ha) | | |
| Species | 0.125 | 0.125 | 0.0625 |
| Cotton | 70 | 15 | 0 |
| Soybean | 0 | 10 | 0 |
| Field Corn | 0 | 5 | 5 |
| Rice | 30 | 20 | 5 |
| Wheat | 5 | 0 | 0 |
| Morningglory | 100 | 80 | 100 |
| Wild Mustard | 100 | 70 | 0 |
| Velvetleaf | 100 | 100 | 95 |
| Barnyardgrass | 60 | 10 | 10 |
| Green Foxtail | 70 | 50 | 0 |
| Johnsongrass | 60 | 40 | 5 |

| | Compound No. | | |
|---|---|---|---|
| | 67 | 68 | 69 |
| | Rate (kg/ha) | | |
| Species | 0.0625 | 0.0625 | 0.25 |
| Cotton | 10 | 0 | 20 |
| Soybean | 0 | 0 | 15 |
| Field Corn | 0 | 0 | 15 |
| Rice | 10 | 0 | 5 |
| Wheat | 5 | 0 | 5 |
| Morningglory | 50 | 5 | 95 |
| Wild Mustard | 50 | 10 | 30 |
| Velvetleaf | 50 | 0 | 100 |
| Barnyardgrass | 5 | 0 | 15 |
| Green Foxtail | 0 | 5 | 0 |
| Johnsongrass | 0 | 0 | 15 |

| | Compound No. | | | |
|---|---|---|---|---|
| | 70 | 72 | 73 | 74 |
| | Rate (kg/ha) | | | |
| Species | 0.25 | 0.25 | 0.25 | 0.5 |
| Cotton | 5 | 5 | 0 | 5 |
| Soybean | 0 | 5 | 0 | 10 |
| Field Corn | 100 | 10 | 0 | 50 |
| Rice | 0 | 10 | 0 | 70 |
| Wheat | 0 | 5 | 0 | 40 |
| Morningglory | 20 | 40 | 5 | 20 |
| Wild Mustard | 0 | 95 | 0 | 100 |
| Velvetleaf | 90 | 100 | 0 | 95 |
| Barnyardgrass | 0 | 30 | 5 | 70 |
| Green Foxtail | 0 | 60 | 0 | 95 |
| Johnsongrass | 0 | 30 | 0 | 95 |

TABLE 4

POSTEMERGENCE HERBICIDAL ACTIVITY (% CONTROL)

| | Compound No. | | |
|---|---|---|---|
| | 1 | 2 | 3 |
| | Rate (kg/ha) | | |
| Species | 0.5 | 0.5 | 0.5 |
| Cotton | 95 | 100 | 100 |
| Soybean | 50 | 40 | 60 |
| Field Corn | 50 | 30 | 60 |
| Rice | 20 | 30 | 40 |
| Wheat | 30 | 40 | 20 |
| Morningglory | 90 | 95 | 100 |
| Wild Mustard | 80 | 95 | 100 |
| Velvetleaf | 100 | 100 | 100 |
| Barnyardgrass | 50 | 30 | 70 |
| Green Foxtail | 50 | 15 | 95 |
| Johnsongrass | 30 | ND | 80 |

| | Compound No. | | |
|---|---|---|---|
| | 4 | 5 | 6 |
| | Rate (kg/ha) | | |
| Species | 0.5 | 0.5 | 0.5 |
| Cotton | 90 | 100 | 100 |
| Soybean | 80 | 80 | 40 |
| Field Corn | 50 | 50 | 40 |
| Rice | 50 | 60 | 15 |
| Wheat | 50 | 80 | 30 |
| Morningglory | 100 | 100 | 90 |
| Wild Mustard | 100 | 100 | 95 |
| Velvetleaf | 100 | 100 | 100 |
| Barnyardgrass | 85 | 90 | 20 |
| Green Foxtail | 50 | 100 | 15 |
| Johnsongrass | ND | 70 | 10 |

| | Compound No. | | |
|---|---|---|---|
| | 7 | 8 | 9 |
| | Rate (kg/ha) | | |
| Species | 0.5 | 0.5 | 0.5 |
| Cotton | 100 | 100 | 100 |
| Soybean | 80 | 50 | 95 |
| Field Corn | 40 | 40 | 50 |
| Rice | 40 | 20 | 20 |
| Wheat | 40 | 40 | 20 |
| Morningglory | 100 | 100 | 100 |
| Wild Mustard | 100 | 100 | 100 |
| Velvetleaf | 100 | 100 | 100 |
| Barnyardgrass | 60 | 40 | 20 |
| Green Foxtail | 30 | 40 | 15 |
| Johnsongrass | 40 | 30 | 40 |

| | Compound No. | | |
|---|---|---|---|
| | 10 | 11 | 12 |
| | Rate (kg/ha) | | |
| Species | 0.5 | 0.5 | 0.5 |
| Cotton | 100 | 95 | 100 |
| Soybean | 60 | 40 | 60 |
| Field Corn | 50 | 50 | 70 |
| Rice | 20 | 15 | 50 |
| Wheat | 40 | 30 | 95 |
| Morningglory | 90 | 90 | 100 |
| Wild Mustard | 95 | 70 | 95 |
| Velvetleaf | 100 | 100 | 100 |
| Barnyardgrass | 70 | 90 | 95 |
| Green Foxtail | 40 | 50 | 85 |
| Johnsongrass | ND | ND | 95 |

| | Compound No. | | |
|---|---|---|---|
| | 13 | 14 | 15 |

TABLE 4-continued

POSTEMERGENCE HERBICIDAL ACTIVITY (% CONTROL)

| | Rate (kg/ha) | | |
|---|---|---|---|
| Species | 0.5 | 0.5 | 0.5 |
| Cotton | 100 | 100 | 100 |
| Soybean | 70 | 85 | 95 |
| Field Corn | 50 | 70 | 90 |
| Rice | 50 | 30 | 90 |
| Wheat | 90 | 90 | 90 |
| Morningglory | 100 | 100 | 100 |
| Wild Mustard | 100 | 100 | 95 |
| Velvetleaf | 100 | 100 | 100 |
| Barnyardgrass | 95 | 95 | 100 |
| Green Foxtail | 100 | 95 | 100 |
| Johnsongrass | 70 | ND | 90 |

| | Compound No. | | |
|---|---|---|---|
| | 16 | 17 | 18 |
| | Rate (kg/ha) | | |
| Species | 0.5 | 0.5 | 0.5 |
| Cotton | 95 | 100 | 100 |
| Soybean | 80 | 100 | 80 |
| Field Corn | 80 | 100 | 70 |
| Rice | 70 | 95 | 80 |
| Wheat | 80 | 100 | 90 |
| Morningglory | 100 | 100 | 95 |
| Wild Mustard | 85 | 100 | 85 |
| Velvetleaf | 100 | 100 | 100 |
| Barnyardgrass | 100 | 95 | 70 |
| Green Foxtail | 95 | 100 | 100 |
| Johnsongrass | 85 | 95 | 80 |

| | Compound No. | | |
|---|---|---|---|
| | 19 | 22 | 23 |
| | Rate (kg/ha) | | |
| Species | 0.5 | 0.5 | 0.5 |
| Cotton | 100 | 100 | 70 |
| Soybean | 90 | 50 | 40 |
| Field Corn | 95 | 85 | 60 |
| Rice | 80 | 40 | 25 |
| Wheat | 100 | 80 | 30 |
| Morningglory | 100 | 100 | 90 |
| Wild Mustard | 80 | 80 | 80 |
| Velvetleaf | 100 | 100 | 90 |
| Barnyardgrass | 60 | 85 | 20 |
| Green Foxtail | 90 | 90 | 40 |
| Johnsongrass | 95 | 95 | 40 |

| | Compound No. | | |
|---|---|---|---|
| | 24 | 25 | 26 |
| | Rate (kg/ha) | | |
| Species | 0.5 | 0.5 | 0.5 |
| Cotton | 100 | 100 | 100 |
| Soybean | 80 | 70 | 90 |
| Field Corn | 60 | 85 | 60 |
| Rice | 10 | 60 | 40 |
| Wheat | 20 | 60 | 40 |
| Morningglory | 100 | 100 | 100 |
| Wild Mustard | 80 | 100 | 95 |
| Velvetleaf | 100 | 100 | 100 |
| Barnyardgrass | 40 | 30 | 70 |
| Green Foxtail | 80 | 70 | 95 |
| Johnsongrass | 60 | 100 | 60 |

| | Compound No. | | |
|---|---|---|---|
| | 27 | 28 | 29 |
| | Rate (kg/ha) | | |
| Species | 0.5 | 0.25 | 0.5 |
| Cotton | 100 | 80 | 100 |
| Soybean | 80 | 60 | 95 |
| Field Corn | 85 | 80 | 100 |
| Rice | 60 | 50 | 95 |
| Wheat | 80 | 60 | 100 |
| Morningglory | 100 | 85 | 100 |
| Wild Mustard | 100 | 90 | 100 |
| Velvetleaf | 100 | 100 | 100 |
| Barnyardgrass | 30 | 30 | 100 |
| Green Foxtail | 60 | 95 | 100 |
| Johnsongrass | 80 | 60 | 100 |

| | Compound No. | | |
|---|---|---|---|
| | 30 | 31 | 33 |
| | Rate (kg/ha) | | |
| Species | 0.25 | 0.5 | 0.25 |
| Cotton | 100 | 100 | 100 |
| Soybean | 85 | 85 | 80 |
| Field Corn | 80 | 70 | 50 |
| Rice | 70 | 60 | 15 |
| Wheat | 100 | 100 | 20 |
| Morningglory | 100 | 100 | 100 |
| Wild Mustard | 100 | 100 | 100 |
| Velvetleaf | 100 | 100 | 100 |
| Barnyardgrass | 50 | 95 | 30 |
| Green Foxtail | 100 | 95 | 15 |
| Johnsongrass | 95 | 95 | 20 |

| | Compound No. | | |
|---|---|---|---|
| | 34 | 36 | 37 |
| | Rate (kg/ha) | | |
| Species | 0.25 | 0.25 | 0.25 |
| Cotton | 100 | 100 | 100 |
| Soybean | 60 | 40 | 70 |
| Field Corn | 30 | 60 | 70 |
| Rice | 20 | 10 | 40 |
| Wheat | 50 | 20 | 20 |
| Morningglory | 100 | 100 | 100 |
| Wild Mustard | 100 | 100 | 100 |
| Velvetleaf | 100 | 100 | 100 |
| Barnyardgrass | 60 | 90 | 50 |
| Green Foxtail | 70 | 100 | 5 |
| Johnsongrass | 50 | 30 | 30 |

| | Compound No. | | |
|---|---|---|---|
| | 39 | 40 | 41 |
| | Rate (kg/ha) | | |
| Species | 0.5 | 0.5 | 0.5 |
| Cotton | 70 | 90 | 100 |
| Soybean | 40 | 40 | 95 |
| Field Corn | 70 | 50 | 70 |
| Rice | 40 | 15 | 70 |
| Wheat | 30 | 40 | 70 |
| Morningglory | 70 | 90 | 100 |
| Wild Mustard | 100 | 80 | 100 |
| Velvetleaf | 100 | 95 | 100 |
| Barnyardgrass | 70 | 80 | 95 |
| Green Foxtail | 80 | 40 | 100 |
| Johnsongrass | 85 | ND | 80 |

| | Compound No. | | |
|---|---|---|---|
| | 42 | 43 | 48 |
| | Rate (kg/ha) | | |
| Species | 0.5 | 0.5 | 0.25 |
| Cotton | 100 | 100 | 100 |
| Soybean | 40 | 100 | 80 |
| Field Corn | 70 | 100 | 80 |
| Rice | 15 | 60 | 40 |
| Wheat | 15 | 95 | 40 |
| Morningglory | 100 | 100 | 100 |
| Wild Mustard | 90 | 100 | 90 |
| Velvetleaf | 100 | 100 | 100 |
| Barnyardgrass | 5 | 95 | 95 |
| Green Foxtail | 10 | 100 | 100 |
| Johnsongrass | 60 | 70 | 90 |

| | Compound No. | | |
|---|---|---|---|
| | 49 | 50 | 51 |
| | Rate (kg/ha) | | |
| Species | 0.25 | 0.25 | 0.25 |
| Cotton | 100 | 100 | 100 |
| Soybean | 70 | 80 | 95 |
| Field Corn | 30 | 80 | 40 |
| Rice | 20 | 40 | 15 |
| Wheat | 15 | 20 | 15 |
| Morningglory | 95 | 100 | 70 |
| Wild Mustard | 70 | 80 | 70 |

TABLE 4-continued

POSTEMERGENCE HERBICIDAL ACTIVITY (% CONTROL)

| | Velvetleaf | 100 | 100 | 100 |
|---|---|---|---|---|
| | Barnyardgrass | 50 | 70 | 15 |
| | Green Foxtail | 85 | 100 | 60 |
| | Johnsongrass | 80 | 85 | 20 |

| | Compound No. | | |
|---|---|---|---|
| | 52 | 53 | 54 |
| | Rate (kg/ha) | | |
| Species | 0.25 | 0.25 | 0.25 |
| Cotton | 95 | 100 | 95 |
| Soybean | 50 | 50 | 70 |
| Field Corn | 60 | 40 | 50 |
| Rice | 15 | 30 | 30 |
| Wheat | 10 | 15 | 30 |
| Morningglory | 50 | 50 | 70 |
| Wild Mustard | 95 | 80 | 100 |
| Velvetleaf | 100 | 100 | 100 |
| Barnyardgrass | 15 | 10 | 15 |
| Green Foxtail | 100 | 50 | 95 |
| Johnsongrass | 5 | 10 | 50 |

| | Compound No. | | |
|---|---|---|---|
| | 57 | 58 | 59 |
| | Rate (kg/ha) | | |
| Species | 0.25 | 0.25 | 0.25 |
| Cotton | 90 | 90 | 100 |
| Soybean | 90 | 90 | 90 |
| Field Corn | 90 | 50 | 100 |
| Rice | 80 | 40 | 95 |
| Wheat | 95 | 60 | 95 |
| Morningglory | 100 | 90 | 100 |
| Wild Mustard | 95 | 100 | 100 |
| Velvetleaf | 100 | 100 | 100 |
| Barnyardgrass | 95 | 60 | 100 |
| Green Foxtail | 100 | 90 | 100 |
| Johnsongrass | 95 | 95 | 100 |

| | Compound No. | | |
|---|---|---|---|
| | 60 | 62 | 63 |
| | Rate (kg/ha) | | |
| Species | 0.25 | 0.0313 | 0.0313 |
| Cotton | 90 | 90 | 95 |
| Soybean | 95 | 70 | 50 |
| Field Corn | 50 | 70 | 60 |
| Rice | 60 | 5 | 10 |
| Wheat | 40 | 10 | 10 |
| Morningglory | 90 | 100 | 100 |
| Wild Mustard | 100 | 80 | 70 |
| Velvetleaf | 100 | 100 | 100 |
| Barnyardgrass | 20 | 50 | 40 |

TABLE 4-continued

POSTEMERGENCE HERBICIDAL ACTIVITY (% CONTROL)

| | Green Foxtail | 40 | 20 | 0 |
|---|---|---|---|---|
| | Johnsongrass | 100 | 20 | 40 |

| | Compound No. | | |
|---|---|---|---|
| | 64 | 65 | 66 |
| | Rate (kg/ha) | | |
| Species | 0.0313 | 0.125 | 0.0625 |
| Cotton | 80 | 95 | 90 |
| Soybean | 50 | 90 | 40 |
| Field Corn | 90 | 40 | 70 |
| Rice | 10 | 30 | 30 |
| Wheat | 10 | 40 | 20 |
| Morningglory | 100 | 100 | 100 |
| Wild Mustard | 85 | 60 | 70 |
| Velvetleaf | 100 | 100 | 100 |
| Barnyardgrass | 60 | 70 | 30 |
| Green Foxtail | 15 | 20 | 15 |
| Johnsongrass | 20 | 60 | 10 |

| | Compound No. | | |
|---|---|---|---|
| | 67 | 68 | 69 |
| | Rate (kg/ha) | | |
| Species | 0.0625 | 0.0625 | 0.25 |
| Cotton | 95 | 40 | 90 |
| Soybean | 40 | 50 | 80 |
| Field Corn | 70 | 60 | 70 |
| Rice | 50 | 5 | 20 |
| Wheat | 40 | 10 | 15 |
| Morningglory | 100 | 70 | 100 |
| Wild Mustard | 100 | 10 | 20 |
| Velvetleaf | 100 | 95 | 100 |
| Barnyardgrass | 70 | 15 | 30 |
| Green Foxtail | 70 | 15 | 50 |
| Johnsongrass | 40 | 10 | 30 |

| | Compound No. | | | |
|---|---|---|---|---|
| | 70 | 72 | 73 | 74 |
| | Rate (kg/ha) | | | |
| Species | 0.25 | 0.25 | 0.25 | 0.5 |
| Cotton | 80 | 100 | 60 | 85 |
| Soybean | 50 | 80 | 30 | 50 |
| Field Corn | 20 | 70 | 60 | 60 |
| Rice | 5 | 15 | 10 | 30 |
| Wheat | 10 | 30 | 10 | 50 |
| Morningglory | 90 | 100 | 30 | 80 |
| Wild Mustard | 50 | 90 | 40 | 95 |
| Velvetleaf | 100 | 100 | 10 | 100 |
| Barnyardgrass | 30 | 10 | 30 | 90 |
| Green Foxtail | 30 | 70 | 70 | 80 |
| Johnsongrass | 20 | 20 | 15 | — |

TABLE 5

Postemergence Herbicidal Activity of Test Compound A - % Control

| | 0.015 lb/acre | | | 0.031 lb/acre | | | 0.063 lb/acre | | |
|---|---|---|---|---|---|---|---|---|---|
| Species | CJM | CRS | SRS | CJM | CRS | SRS | CJM | CRS | SRS |
| Velvetleaf | — | 100 | 100 | — | 100 | 100 | — | 100 | 100 |
| Smooth Pigweed | — | — | 93 | — | — | 100 | — | — | 100 |
| Spleen Amaranth | 62 | — | — | 82 | — | — | 95 | — | — |
| Redroot Pigweed | — | 85 | 95 | — | 85 | 100 | — | 100 | 100 |
| Common Ragweed | — | 38 | — | — | 56 | — | — | 86 | — |
| Giant Ragweed | — | 39 | — | — | 36 | — | — | 81 | — |
| Hairy Beggarticks | 59 | — | — | 74 | — | — | 84 | — | — |
| Sicklepod | 58 | — | 0 | 75 | — | 8 | 89 | — | 16 |
| Lambsquarters | — | 93 | — | — | 98 | — | — | 100 | — |
| Jimsonweed | 92 | — | 98 | 97 | — | 100 | 98 | — | 100 |
| Florida beggarweed | — | — | 2 | — | — | 13 | — | — | 50 |
| Wild Poinsettia | 78 | — | — | 83 | — | — | 98 | — | — |
| Ivyleaf Morningglory | — | 86 | 40 | — | 98 | 86 | — | 99 | 100 |
| Morningglory (SP) | 61 | — | — | 83 | — | — | 98 | — | — |
| Kochia | — | 86 | — | — | 99 | — | — | 99 | — |
| Southern Sida | 77 | — | — | 91 | — | — | 99 | — | — |
| Prickly Sida | — | — | 5 | — | — | 45 | — | — | 95 |
| Cocklebur | 79 | 44 | 95 | 92 | 91 | 99 | 97 | 98 | 100 |
| Southern Sandbur | 35 | — | — | 38 | — | — | 42 | — | — |

TABLE 5-continued

Postemergence Herbicidal Activity of Test Compound A - % Control

| | 0.015 lb/acre | | | 0.031 lb/acre | | | 0.063 lb/acre | | |
|---|---|---|---|---|---|---|---|---|---|
| Species | CJM | CRS | SRS | CJM | CRS | SRS | CJM | CRS | SRS |
| Large crabgrass | 36 | 54 | 0 | 36 | 41 | 0 | 37 | 55 | 0 |
| Barnyardgrass | — | 13 | 1 | — | 18 | 6 | — | 29 | 10 |
| Junglerice | 46 | — | — | 57 | — | — | 54 | — | — |
| Goosegrass | 38 | — | — | 47 | — | — | 40 | — | — |
| Giant foxtail | — | 75 | 0 | — | 83 | 1 | — | 73 | 8 |
| Green foxtail | — | 81 | 1 | — | 75 | 0 | — | 80 | 11 |
| Johnsongrass | 47 | 16 | 1 | 44 | 19 | 6 | 43 | 34 | 11 |

TABLE 6

Postemergence Herbicidal Activity of Test Compound B - % Control

| | 0.03 lb/acre | | | 1.0 lb/acre | | |
|---|---|---|---|---|---|---|
| Species | CJM | CRS | SRS | CJM | CRS | SRS |
| Velvetleaf | — | 74 | 5 | — | 100 | 75 |
| Smooth Pigweed | — | — | 16 | — | — | 88 |
| Spleen Amaranth | 46 | — | — | 95 | — | — |
| Redroot Pigweed | — | 76 | 16 | — | 100 | 95 |
| Common Ragweed | — | 100 | — | — | 100 | — |
| Giant Ragweed | — | 99 | — | — | 100 | — |
| Hairy Beggarticks | 87 | — | — | 96 | — | — |
| Sicklepod | 98 | — | 83 | 100 | — | 91 |
| Lambsquarters | — | 86 | — | — | 100 | — |
| Jimsonweed | 52 | — | 10 | 99 | — | 95 |
| Florida beggarweed | — | — | 60 | — | — | 98 |
| Wild Poinsettia | 84 | — | — | 100 | — | — |
| Ivy Leaf Morningglory | — | 84 | 1 | — | 98 | 84 |
| Morningglory(sp) | 65 | — | — | 98 | — | — |
| Kochia | — | 76 | — | — | 100 | — |
| Southern Sida | 73 | — | — | 100 | — | — |
| Prickly Sida | — | — | 23 | — | — | 64 |
| Cocklebur | 86 | 91 | 91 | 95 | 100 | 94 |
| Southern Sandbur | 50 | — | — | 96 | — | — |
| Large Crabgrass | 52 | 86 | 85 | 94 | 96 | 100 |
| Barnyardgrass | — | 85 | 85 | — | 100 | 100 |
| Junglerice | 75 | — | — | 97 | — | — |
| Goosegrass | 58 | — | — | 90 | — | — |
| Giant Foxtail | — | 94 | 91 | — | 100 | 100 |
| Green Foxtail | — | 86 | 90 | — | 100 | 100 |
| Johnsongrass | 95 | 78 | 80 | 99 | 95 | 100 |

TABLE 7

Postemergence Herbicidal Activity of the Combination of Test Compounds A and B - % Control

| | Application Rates in Pounds per Acre | | | | | | | | |
|---|---|---|---|---|---|---|---|---|---|
| | A = 0.015/ B = 0.3 | | | A = 0.031/ B = 0.3 | | | A = 0.063/ B = 0.3 | | |
| Species | CJM | CRS | SRS | CJM | CRS | SRS | CJM | CRS | SRS |
| Velvetleaf | — | 95 | 100 | — | 98 | 100 | — | 100 | 100 |
| Smooth Pigweed | — | — | 100 | — | — | 100 | — | — | 100 |
| Spleen Amaranth | 82 | — | — | 69 | — | — | 95 | — | — |
| Redroot Pigweed | — | 75 | 99 | — | 86 | 100 | — | 96 | 100 |
| Common Ragweed | — | 100 | — | — | 100 | — | — | 100 | — |
| Giant Ragweed | — | 96 | — | — | 95 | — | — | 99 | — |
| Hairy Beggarticks | 92 | — | — | 94 | — | — | 94 | — | — |
| Sicklepod | 100 | — | 93 | 100 | — | 85 | 100 | — | 88 |
| Lambsquarters | — | 100 | — | — | 100 | — | — | 100 | — |
| Jimsonweed | 100 | — | 98 | 100 | — | 98 | 100 | — | 100 |
| Florida Beggarweed | — | — | 73 | — | — | 80 | — | — | 87 |
| Wild Poinsettia | 94 | — | — | 98 | — | — | 100 | — | — |
| Ivy Leaf Morningglory | — | 97 | 45 | — | 96 | 86 | — | 98 | 100 |
| Morningglory(sp) | 91 | — | — | 91 | — | — | 97 | — | — |
| Kochia | — | 74 | — | — | 92 | — | — | 99 | — |
| Southern Sida | 96 | — | — | 95 | — | — | 100 | — | — |
| Prickly Sida | — | — | 88 | — | — | 98 | — | — | 99 |
| Cocklebur | 97 | 85 | 95 | 95 | 99 | 98 | 99 | 99 | 96 |
| Southern Sandbur | 60 | — | — | 60 | — | — | 77 | — | — |
| Large Crabgrass | 73 | 85 | 80 | 64 | 93 | 83 | 69 | 96 | 88 |
| Barnyardgrass | — | 75 | 85 | — | 89 | 90 | — | 91 | 93 |
| Junglerice | 78 | — | — | 78 | — | — | 78 | — | — |
| Goosegrass | 67 | — | — | 75 | — | — | 81 | — | — |
| Giant Foxtail | — | 91 | 94 | — | 99 | 94 | — | 96 | 94 |
| Green Foxtail | — | 94 | 88 | — | 98 | 85 | — | 94 | 93 |
| Johnsongrass | 91 | 80 | 87 | 95 | 89 | 89 | 99 | 85 | 98 |

I claim:

1. A herbicidal composition comprising a synergistic herbicidally effective amount of the combination of a phenylpropionate compound of the formula

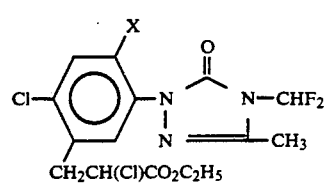

wherein X is chlorine or fluorine, or mixtures thereof, and monoammonium 2-amino-4-[(hydroxy)methylphosphinyl]butanoate in admixture with a suitable carrier.

2. The composition of claim 1 wherein the weight ratio of the phenylpropionate to butanoate is from about 1:25 to 1:1.

3. A method of controlling undesired plant growth which comprises applying to the locus where control is desired a synergistic herbicidally effective amount of the composition of claim 1.

4. A herbicidal composition comprising a synergistic herbicidally effective amount of the combination of a phenylpropionate compound of the formula

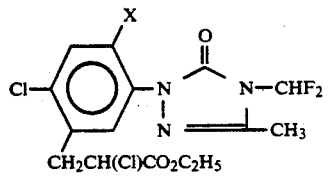

wherein X is chlorine or fluorine, or mixtures thereof, and bialaphos in admixture with a suitable carrier.

5. The composition of claim 4 wherein the weight ratio of the phenylpropionate to bialaphos is from about 1:25 to 1:1.

6. A method of controlling undesired plant growth which comprises applying to the locus where control is desired a synergistic herbicidally effective amount of the composition of claim 4.

* * * * *